United States Patent
Ibrahim et al.

(10) Patent No.: US 6,900,219 B2
(45) Date of Patent: May 31, 2005

(54) ABCA-1 ELEVATING COMPOUNDS

(75) Inventors: Prabha Ibrahim, Mountain View, CA (US); Michael Campbell, Durham, NC (US); Robert Jiang, Cupertino, CA (US); Christopher Morrison, Sunnyvale, CA (US); Kevin Shenk, Palo Alto, CA (US); William Shirley, La Jolla, CA (US); Jeff Zablocki, Mountain View, CA (US); Dmitry Koltun, Millbrae, CA (US); Reina Natero, Menlo Park, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 10/407,875

(22) Filed: Apr. 4, 2003

(65) Prior Publication Data

US 2003/0220356 A1 Nov. 27, 2003

Related U.S. Application Data

(60) Provisional application No. 60/370,122, filed on Apr. 4, 2002.

(51) Int. Cl.⁷ .................. A61K 31/517; A61K 31/425; A61K 31/415

(52) U.S. Cl. ............................ 514/266.1; 514/266.2; 514/365; 514/367; 514/406

(58) Field of Search .................... 514/266.1, 266.2, 514/365, 367, 406

(56) References Cited

U.S. PATENT DOCUMENTS

| | | | |
|---|---|---|---|
| 6,548,548 B2 * | 4/2003 | Campbell et al. | 514/617 |
| 2002/0082257 A1 * | 6/2002 | Ibrahim et al. | 514/217.12 |
| 2002/0128266 A1 * | 9/2002 | Campbell et al. | 514/245 |
| 2003/0069234 A1 * | 4/2003 | Medina et al. | 514/227.8 |

FOREIGN PATENT DOCUMENTS

| | | |
|---|---|---|
| WO | WO 01/16114 A2 | 3/2001 |
| WO | WO 02/083143 A1 | 10/2002 |
| WO | WO 01/81346 A2 | 11/2002 |

* cited by examiner

*Primary Examiner*—Raymond J. Henley, III
(74) *Attorney, Agent, or Firm*—Brian Lewis; J. Elin Hartrum

(57) ABSTRACT

The present invention provides compounds that elevate cellular expression of the ABCA-1 gene, promoting cholesterol efflux from cells and increasing HDL levels in the plasma of a mammal, in particular humans. The compounds are useful for treating coronary artery disease.

48 Claims, No Drawings

ABCA-1 ELEVATING COMPOUNDS

Priority is claimed to U.S. Provisional Patent Application Ser. No. 60/370,122, filed Apr. 4, 2002, the complete disclosure of which is hereby incorporated by reference.

FIELD OF THE INVENTION

The present invention relates to compounds useful for raising cellular ABCA-1 production in mammals, and to methods of using such compounds in the treatment of coronary artery diseases. The invention also relates to pharmaceutical compositions containing such compounds.

BACKGROUND OF THE INVENTION

Cholesterol is essential for the growth and viability of higher organisms. It is a lipid that modulates the fluidity of eukaryotic membranes, and is the precursor to steroid hormones such as progesterone, testosterone, and the like. Cholesterol can be obtained from the diet, or synthesized internally in the liver and the intestines. Cholesterol is transported in body fluids to specific targets by lipoproteins, which are classified according to increasing density. For example, low density lipoprotein cholesterol (LDL) is responsible for transport of cholesterol to and from the liver and to peripheral tissue cells, where LDL receptors bind LDL, and mediate its entry into the cell.

Although cholesterol is essential to many biological processes in mammals, elevated serum levels of LDL cholesterol are undesirable, in that they are known to contribute to the formation of atherosclerotic plaques in arteries throughout the body, which may lead, for example, to the development of coronary artery diseases. Conversely, elevated levels of high density lipoprotein cholesterol (HDL-C) have been found, based upon human clinical data, and animal model systems, to protect against development of coronary diseases.

In general, excess cholesterol is removed from the body by a pathway involving high density lipoproteins (HDLs). Cholesterol is "effluxed" from cells by one of two processes—either by passive transfer to mature HDL, or an active transfer to apolipoprotein A-1. The latter process is mediated by a protein known as ATP binding cassette transporter 1 (ABC-1, or alternatively referenced as ABCA-1). In the latter process, lipid-poor HDL precursors acquire phospholipid and cholesterol, which leads to increased plasma levels of mature HDL particles. HDL cholesterol is eventually transported to the liver in a process known as "reverse cholesterol transport", where it is either recycled or excreted as bile.

One method of treatment aimed at reducing the risk of formation of atherosclerotic plaques in arteries relates to decreasing plasma lipid levels. Such a method includes diet changes, and/or treatment with drugs such as derivatives of fibric acid (clofibrate, gemfibrozil, and fenofibrate), nicotinic acid, and HMG-CoA reductase inhibitors, such as mevinolin, mevastatin, pravastatin, simvastatin, fluvastatin, and lovastatin, which reduce plasma LDL cholesterol levels by either inhibiting the intracellular synthesis of cholesterol or inhibiting the uptake via LDL receptors. In addition, bile acid-binding resins, such as cholestyrine, colestipol and probucol decrease the level of LDL-cholesterol by reducing intestinal uptake and increasing the catabolism of LDL-cholesterol in the liver.

It is desired to provide alternative therapies aimed at reducing the risk of formation of atherosclerotic plaques in arteries, especially in individuals deficient in the removal of cholesterol from artery walls via the HDL pathway. Given that HDL levels are generally related to the expression of ABCA-1, one method of increasing HDL levels would be to increase the expression of ABCA-1. Accordingly, it is desired to provide compounds that are potent stimulators of the expression of ABCA-1 in mammals, thus increasing cholesterol efflux and raising HDL cholesterol levels in blood. This would be useful for the treatment of various disease states characterized by low HDL levels, in particular coronary artery disease.

It has also been shown that a combination of a drug that decreases LDL cholesterol levels and a drug that increases HDL cholesterol is beneficial; see, for example, Arterioscler., Thromn., Vasc. Biol. (2001), 21(8), 1320–1326, by Marian C. Cheung et al. Accordingly, it is also desired to provide a combination of a compound that stimulates the expression of ABCA-1 with a compound that lowers LDL cholesterol levels.

It should be noted it has also been shown that raising ABCA-1 production in macrophages locally reduces cholesterol deposition in coronary arteries without significantly raising plasma HDL cholesterol. In this instance, raising ABCA-1 expression is beneficial even in the absence of increased HDL cholesterol.

SUMMARY OF THE INVENTION

It is an object of this invention to provide compounds that elevate cellular expression of the ABCA-1 gene, thus increasing the level of high density lipoprotein cholesterol (HDL-C) in plasma and lowering lipid levels in a mammal. Accordingly, in a first aspect, the invention relates to compounds of Formula I:

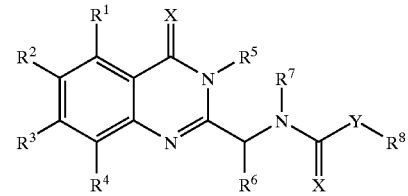

Formula I wherein:

$R^1$, $R^2$, $R^3$ and $R^4$ are independently hydrogen, optionally substituted alkyl, optionally substituted alkenyl, optionally substituted alkynyl, optionally substituted alkoxy, optionally substituted cycloalkyl, acyl, acylamino, acyloxy, optionally substituted amino, aminocarbonyl, cyano, halogen, hydroxy, carboxy, carboxyalkyl, optionally substituted aryl, optionally substituted aryloxy, optionally substituted heteroaryl, optionally substituted heterocyclyl, $SO_2NR^aR^b$, —SO-alkyl, —SO-aryl, —SO-heteroaryl, —$SO_2$-alkyl, $SO_2$-aryl, and trifluoromethyl;

in which $R^a$ and $R^b$ are independently hydrogen, lower alkyl, or cycloalkyl;

$R^5$ is hydrogen, optionally substituted alkyl, optionally substituted alkenyl, optionally substituted alkynyl, optionally substituted cycloalkyl, optionally substituted heterocyclyl, optionally substituted aryl, or optionally substituted heteroaryl;

$R^6$ is hydrogen, optionally substituted alkyl or optionally substituted cycloalkyl;

$R^7$ is hydrogen, optionally substituted alkyl, optionally substituted alkenyl, optionally substituted alkynyl, optionally substituted cycloalkyl, optionally substituted heterocyclyl, optionally substituted aryl, or optionally substituted heteroaryl;

$R^8$ is optionally substituted alkyl, optionally substituted alkenyl, optionally substituted alkynyl, optionally substituted cycloalkyl, optionally substituted heterocyclyl, optionally substituted aryl, or optionally substituted heteroaryl;

X is independently oxygen or sulfur; and

Y is oxygen, —$NR^9$—, or a covalent bond, in which $R^9$ is hydrogen or lower alkyl.

In a second aspect, the invention relates to compounds of Formula II:

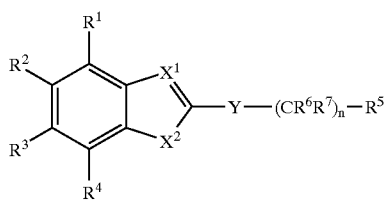

Formula II wherein:

n is 0, 1, 2, or 3;

$R^1$, $R^2$, $R^3$ and $R^4$ are hydrogen, optionally substituted alkyl, optionally substituted alkenyl, optionally substituted alkynyl, optionally substituted alkoxy, optionally substituted cycloalkyl, acyl, acylamino, acyloxy, amino, aminocarbonyl, cyano, halogen, hydroxy, carboxy, carboxyalkyl, optionally substituted aryl, optionally substituted aryloxy, optionally substituted heteroaryl, optionally substituted heterocyclyl, $SO_2NR^aR^b$, —SO-alkyl, —SO-aryl, —SO-heteroaryl, —$SO_2$-alkyl, $SO_2$-aryl, and trifluoromethyl;

in which $R^a$ and $R^b$ are independently hydrogen, lower alkyl, or cycloalkyl;

$R^5$ is optionally substituted alkyl, optionally substituted cycloalkyl, optionally substituted aryl, optionally substituted heteroaryl, or optionally substituted heterocyclyl;

$R^6$ and $R^7$ are independently hydrogen, optionally substituted lower alkyl, optionally substituted cycloalkyl, halo, hydroxy, or cyano, with the proviso that $R^6$ and $R^7$ cannot both be hydroxy; and with the proviso that when $R^6$ or $R^7$ are hydroxy, halo, or cyano they cannot be adjacent to a nitrogen atom; or $X^1$ is nitrogen or —$C(R^8)$—, in which $R^8$ is hydrogen, hydroxy, halo, cyano, optionally substituted lower alkyl, optionally substituted lower alkoxy, optionally substituted cycloalkyl, optionally substituted aryl, optionally substituted heteroaryl, or optionally substituted heterocyclyl;

$X^2$ is oxygen, sulfur, or —$NR^9$—;

Y is —$N(R^9)$—, —$N(R^9)$—$C(T)$—, —$C(T)$—$N(R^9)$—, —$N(R^9)$—$C(T)$—$N(R^9)$—, $N(R^9)SO$—, or a covalent bond;

in which T is oxygen or sulfur and $R^9$ at each occurrence is hydrogen or lower alkyl optionally substituted by hydroxy, halo, or —$CO(O)R$, in which R is hydrogen, optionally substituted lower alkyl, optionally substituted cycloalkyl, optionally substituted heterocyclyl, optionally substituted aryl, or optionally substituted heteroaryl, with the proviso that when $R^9$ is lower alkyl substituted by hydroxy, halo, or cyano, such substituents cannot be adjacent to a nitrogen atom.

In a third aspect, the invention relates to compounds of Formula III:

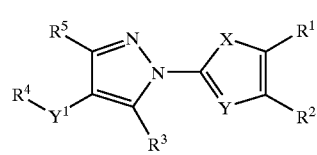

Formula III wherein:

$R^1$ and $R^2$ are independently hydrogen, optionally substituted lower alkyl, optionally substituted cycloalkyl, optionally substituted alkoxy, optionally substituted heterocyclyl, optionally substituted aryl, optionally substituted heteroaryl, or —$CO_2R$, in which R is hydrogen, optionally substituted lower alkyl, or optionally substituted aryl;

$R^3$ and $R^5$ are hydrogen, trifluoromethyl, optionally substituted lower alkyl, or optionally substituted cycloalkyl;

$R^4$ is optionally substituted alkyl, optionally substituted cycloalkyl, optionally substituted heterocyclyl, optionally substituted aryl, or optionally substituted heteroaryl, $Y^1$ is —$N(R^7)$—, —$N(R^7)$—$C(T)$—, —$C(T)$—$N(R^7)$—, —$N(R^7)$—$C(T)$—$N(R^7)$—,—$N(R^7)SO_2$—, or a covalent bond;

in which $R^7$ is hydrogen, optionally substituted alkyl, or optionally substituted aryl; or $R^4$ and $R^7$ when taken together with the nitrogen to which they are attached represents —Z—C(O)—$R^8$, in which Z is 1,4-piperazinyl optionally substituted with lower alkyl and $R^8$ is optionally substituted alkyl or optionally substituted aryl;

T is oxygen or sulfur;

X is —$NR^a$—, oxygen, or sulfur; in which $R^a$ is hydrogen, lower alkyl, or cycloalkyl; and Y is nitrogen or —$CH(R^6)$—, in which $R^6$ is hydrogen, hydroxy, halo, optionally substituted lower alkyl, optionally substituted lower alkoxy, optionally substituted cycloalkyl, optionally substituted aryl, optionally substituted heteroaryl, or optionally substituted heterocyclyl.

In a fourth aspect, the invention relates to compounds of Formula IV:

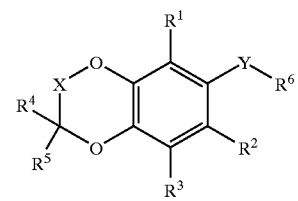

Formula IV wherein:

$R^1$, $R^2$, and $R^3$ are independently hydrogen, optionally substituted alkyl, optionally substituted alkenyl, optionally substituted alkynyl, optionally substituted alkoxy, optionally substituted cycloalkyl, acyl, acylamino, acyloxy, amino, aminocarbonyl, cyano, halogen, hydroxy, carboxy, carboxyalkyl, optionally substituted aryl, optionally substituted aryloxy, optionally substituted heteroaryl, optionally substituted heterocyclyl, $SO_2NR^aR^b$, —SO-alkyl, —SO-aryl, —SO-heteroaryl, —$SO_2$-alkyl, $SO_2$-aryl, and trifluoromethyl;

in which $R^a$ and $R^b$ are independently hydrogen, lower alkyl, or cycloalkyl;

$R^4$ and $R^5$ are independently hydrogen, optionally substituted alkyl, optionally substituted cycloalkyl, halo, cyano, or hydroxy, with proviso that $R^4$ and $R^5$ are not both hydroxy or cyano; or $R^4$ and $R^5$ when taken together with the carbon atom to which they are attached represent carbonyl;

$R^6$ is optionally substituted alkyl, optionally substituted cycloalkyl, optionally substituted aryl, optionally substituted heteroaryl, or optionally substituted heterocyclyl;

X is a covalent bond or —CHR$^7$—, in which $R^7$ is hydrogen, hydroxy, halo, optionally substituted lower alkyl, optionally substituted lower alkoxy, optionally substituted cycloalkyl, optionally substituted aryl, optionally substituted heteroaryl, or optionally substituted heterocyclyl Y is —N(R$^8$)—, —N(R$^8$)—C(T)—, —C(T)—N(R$^8$)—, —N(R$^8$)—C(T)—N(R$^8$)—, or —N(R$^8$)SO$_2$—;

in which $R^8$ at each occurrence is hydrogen, lower alkyl optionally substituted by hydroxy, halo, —CO(O)R, in which R is hydrogen, lower alkyl, cycloalkyl, aryl, or heteroaryl, all of which may be optionally substituted, and T is oxygen or sulfur; or $R^8$ and $R^6$ when taken together with the atoms to which they are attached is a heterocyclyl group.

In a fifth aspect, the invention relates to compounds of Formula V:

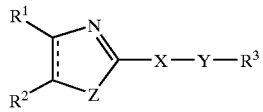

Formula V wherein:

$R^1$ is hydrogen, hydroxy, optionally substituted lower alkyl, optionally substituted alkoxy, optionally substituted aryl, optionally substituted heteroaryl, or —CO$_2$R, in which R is hydrogen, optionally substituted lower alkyl, or optionally substituted aryl; or $R^1$ and the dotted line when taken together with the carbon atom to which they are attached represent carbonyl; or $R^1$ and $R^2$ when taken together with the carbons to which they are attached form an optionally substituted 6-membered aromatic ring;

$R^2$ is hydrogen or lower alkyl;

$R^3$ is optionally substituted cycloalkyl, optionally substituted aryl, or optionally substituted heteroaryl;

X is —NR$^4$R$^5$, —C(T)—NR$^4$—, —NR$^4$C(T)—, —NR$^4$CSO$_2$—, or —NR$^4$—C(T)NR$^4$;

in which T is oxygen or sulfur, $R^4$ is hydrogen, optionally substituted lower alkyl, or optionally substituted cycloalkyl, and $R^5$ is optionally substituted aryl;

Y is optionally substituted lower alkylene or a covalent bond;

Z is oxygen, sulfur, or —NH—; and the dotted line represents an optional double bond.

In a sixth aspect, the invention relates to a method for using the compounds of Formula I, II, III, IV, and V in the treatment of a disease or condition in a mammal that can be treated with a compound that elevates serum levels of HDL cholesterol, comprising administering to a mammal in need thereof a therapeutically effective dose of a compound of Formula I, II, III, IV, or V. Such diseases include, but are not limited to, diseases of the artery, in particular coronary artery disease, and diabetes.

In a seventh aspect, the invention relates to a method for using the compounds of Formula I, II, III, IV, and V in the treatment of a disease or condition in a mammal that can be treated with a compound that promotes cholesterol efflux from cells, comprising administering to a mammal in need thereof a therapeutically effective dose of a compound of Formula I, II, III, IV, or V. Such diseases include, but are not limited to, diseases of the artery, in particular coronary artery disease, and diabetes.

In an eighth aspect, the invention relates to a method for using the compounds of Formula I, II, III, IV, and V in the treatment of a disease or condition characterized by low HDL-C in a mammal that can be usefully treated with a compound that elevates serum levels of HDL-C, comprising administering to a mammal in need thereof a therapeutically effective dose of a compound of Formula I, II, III, IV, or V. Such diseases include, but are not limited to, diseases of the artery, in particular coronary artery disease, and diabetes.

A ninth aspect of this invention relates to pharmaceutical formulations, comprising a therapeutically effective amount of a compound of Formula I, II, III, IV, or V, and at least one pharmaceutically acceptable excipient.

Of the compounds of Formula I, one preferred class of compounds that elevate cellular expression of the ABCA-1 gene includes those in which $R^1$, $R^2$ and $R^4$ are hydrogen, $R^3$ is hydrogen or halogen, and X is oxygen. Within this class preferred compounds include those in which $R^6$ and $R^7$ are independently optionally substituted lower alkyl, and Y is —NR$^9$, in which $R^9$ is hydrogen. One preferred group within this class includes compounds in which $R^5$ is optionally substituted lower alkyl. Another preferred group includes compounds in which $R^5$ is optionally substituted aryl, especially those in which $R^5$ is optionally substituted phenyl or optionally substituted naphthyl, and $R^6$ is methyl or ethyl. Particularly pteferred compounds include those in which $R^7$ is n-propyl, 3-methylbutyl, 2-methoxyethyl, or benzyl, $R^5$ is naphthyl, 3,4-dimethylphenyl, 4-methylphenyl, or 4-chlorophenyl, and $R^8$ is n-butyl, naphthyl, 2,6-dimethylphenyl, 2-methylphenyl, 3-fluorophenyl, 4-methylphenyl, 4-chlorophenyl, 3-trifluoromethylphenyl, 3-methoxyphenyl, 4-methoxyphenyl, or 2,4-difluorophenyl.

Of the compounds of Formula III, one preferred class of compounds that elevate cellular expression of the ABCA-1 gene includes those in which X is sulfur, Y is nitrogen, $R^1$ and $R^5$ are hydrogen and $R^2$ is optionally substituted aryl. A preferred class of compounds includes those in which $R^3$ is optionally substituted lower alkyl, especially those in which $Y^1$ is —C(T)—N(R$^7$)—, in which T is oxygen and $R^7$ is hydrogen. Particularly preferred are those compounds in which $R^4$ is optionally substituted lower alkyl or optionally substituted cycloalkyl.

Of the compounds of Formula V, one preferred class of compounds that elevate cellular expression of the ABCA-1 gene includes those in which X is —NR$^4$C(T)—, in which $R^4$ is hydrogen and T is oxygen, Y is a covalent bond, Z is sulfur, and the dotted line represents a double bond. One preferred group includes those compounds in which $R^3$ is optionally substituted cycloalkyl or optionally substituted aryl. One preferred subgroup includes those compounds in which $R^1$ is phenyl or naphthyl and $R^2$ is hydrogen, especially those in which $R^3$ is optionally substituted phenyl. More preferred are those compounds in which $R^3$ is 4-cyanophenyl, 4-hydroxyphenyl, or 3,4-dimethylphenyl. Another preferred subgroup includes those compounds in which $R^1$ is hydrogen and $R^2$ is optionally substituted phenyl, especially those in which $R^3$ is optionally substituted cycloalkyl and R is phenyl, 2-chlorophenyl or 4-fluorophenyl and $R^3$ is cyclopropyl. Another preferred class include those compounds in which the dotted line represents a double bond and $R^1$ and $R^2$ taken together with the carbons to which they are attached form an optionally substituted 6-membered carbocyclic aromatic ring, especially those compounds in which the aromatic ring is optionally substituted with halogen or lower alkylsulfonyl. Within this subgroup a preferred subclass includes those compounds in which the aromatic carbocyclic group is optionally substituted with halo, particularly chloro, and $R^3$ is optionally substituted aryl, particularly 3-cyanophenyl, 4-cyanophenyl, or 4-methoxyphenyl. Another preferred subclass includes those compounds in which $R^3$ is optionally substituted heteroaryl, in particular 2-thienyl.

At present, preferred compounds that elevate cellular expression of the ABCA-1 gene include the following:

3,5,5-trimethyl-hexanoic acid benzyl-[1-(4-oxo-3-propyl-3,4-dihydro-quinazolin-2-yl)propyl]-amide;
N-(2-methylpropyl)(naphthylamino)-N-[(3-(2-naphthyl)-4-oxo(3-hydroquinazolin-2-yl))ethyl]carboxamide;
[(4-chlorophenyl)amino]-N-(2-methylpropyl)-N-[(3-(2-naphthyl)-4-oxo(3-hydroquinazolin-2-yl))ethyl] carboxamide;
N-(2-methylpropyl)-N-[(3-(2-naphthyl)-4-oxo(3-hydroquinazolin-2-yl))ethyl]{[3-(trifluoromethyl)phenyl] amino}carboxamide;
(butylamino)-N-{[7-chloro-3-(4-methylphenyl)-4-oxo(3-hydroquinazolin-2-yl)]ethyl}-N-(3-methylbutyl) carboxamide;
N-{[7-chloro-3-(4-methylphenyl)-4-oxo(3-hydroquinazolin-2-yl)]ethyl}[(3-methoxyphenyl)amino]-N-propylcarboxamide;
[(2,4-difluorophenyl)amino]-N-[2-(dimethylamino)ethyl]-N-[(3-(2-naphthyl)-4-oxo(3-hydroquinazolin-2-yl))ethyl] carboxamide;
N-{[3-(3,4-dimethylphenyl)-4-oxo(3-hydroquinazolin-2-yl)]propyl}[(4-methoxyphenyl)amino]-N-benzylcarboxamide;
[(3-fluorophenyl)amino]-N-[(3-(2-naphthyl)-4-oxo(3-hydroquinazolin-2-yl))ethyl]-N-propylcarboxamide;
[(2,4-difluorophenyl)amino]-N-{[3-(4-chlorophenyl)-4-oxo(3-hydroquinazolin-2-yl)]propyl}-N-(2-methoxyethyl) carboxamide;
5-isopropyl-1-(4-p-tolyl-thiazol-2-yl)-1H-pyrazole-4-carboxylic acid (3-methyl-butyl)-amide;
5-isopropyl-1-(4-p-tolyl-thiazol-2-yl)-1H-pyrazole-4-carboxylic acid cyclopropylamide;
5-isopropyl-1-(4-p-tolyl-thiazol-2-yl)-1H-pyrazole-4-carboxylic acid (1-phenyl-ethyl)-amide;
5-ethyl-1-[4-(4-methoxyphenyl)-thiazol-2-yl)]-1H-pyrazole-4-carboxylic acid (furan-2-ylmethyl)-amide;
5-ethyl-1-(4-p-tolyl-thiazol-2-yl)-1H-pyrazole-4-carboxylic acid (furan-2-ylmethyl)-amide;
5-methyl-1-(4-p-tolyl-thiazol-2-yl)-1H-pyrazole-4-carboxylic acid (2-phenylethyl)-amide;
N-[6-(methylsulfonyl)benzothiazol-2-yl]-2-thienylcarboxamide;
(4-cyanophenyl)-N-(4-naphthalen-2-yl-thiazol-2-yl)-carboxamide;
N-benzothiazol-2-yl(4-cyanophenyl)carboxamide;
cyclopropyl-N-(5-phenyl(1,3-thiazol-2-yl))carboxamide;
(4-methoxyphenyl)-N-(4-phenyl(1,3-thiazol-2-yl)) carboxamide;
(4-cyanophenyl)-N-(4-phenyl(1,3-thiazol-2-yl)) carboxamide;
(3,4-dimethylphenyl)-N-(4-phenyl(1,3-thiazol-2-yl)) carboxamide;
N-(4-chlorobenzothiazol-2-yl)(4-cyanophenyl) carboxamide;
N-benzothiazol-2-yl(3-cyanophenyl)carboxamide;
N-(4-chlorobenzothiazol-2-yl)(3-cyanophenyl) carboxamide;
N-(6-chlorobenzothiazol-2-yl)(3-cyanophenyl) carboxamide;
cyclopropyl-N-[5-(4-fluorophenyl)(1,3-thiazol-2-yl)] carboxamide; and
N-[5-(2-chlorophenyl)(1,3-thiazol-2-yl)] cyclopropylcarboxamide.

Many of the compounds related to the present invention are commercially available from, for example, ComGenex, South San Francisco, USA, or Maybridge Chemicals, England.

Definitions and General Parameters

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-pentyl, 2-methylbutyl, n-hexyl, n-decyl, tetradecyl, and the like.

The term "substituted alkyl" refers to:

1) an alkyl group as defined above, having from 1 to 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or 2) an alkyl group as defined above that is interrupted by 1–5 atoms or groups independently chosen from oxygen, sulfur and —NR$_a$—, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or 3) an alkyl group as defined above that has both from 1 to 5 substituents as defined above and is also interrupted by 1–5 atoms or groups as defined above.

The term "lower alkyl" refers to a monoradical branched or unbranched saturated hydrocarbon chain having from 1 to 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1 to 3 substituents, as defined for substituted alkyl, or a lower alkyl group as defined above that is interrupted by 1–5 atoms as defined for substituted alkyl, or a lower alkyl group as defined above that has both from 1 to 5 substituents as defined above and is also interrupted by 1–5 atoms as defined above.

The term "alkylene" refers to a diradical of a branched or unbranched saturated hydrocarbon chain, preferably having from 1 to 20 carbon atoms, preferably 1–10 carbon atoms, more preferably 1–6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain, preferably having from 1 to 6 carbon atoms.

The term "substituted alkylene" refers to:
(1) an alkylene group as defined above having from 1 to 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or
(2) an alkylene group as defined above that is interrupted by 1–5 atoms or groups independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or
(3) an alkylene group as defined above that has both from 1 to 5 substituents as defined above and is also interrupted by 1–20 atoms as defined above. Examples of substituted alkylenes are chloromethylene (—CH(Cl)—), amino ethylene (—CH(NH$_2$)CH$_2$—), methylaminoethylene (—CH(NHMe)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y-Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexyloxy, 1,2-dimethylbutoxy, trifluoromethoxy, and the like.

The term "alkylthio" refers to the group R-S-, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1–6, preferably 1, double bond (vinyl). Preferred alkenyl groups include ethenyl or vinyl (—CH═CH$_2$), 1-propylene or allyl (—CH$_2$CH═CH$_2$), isopropylene (—C(CH$_3$)═CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, alkoxy, halogen, CF3, amino, substituted amino, cyano, or —S(O)$_n$R, in which R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1–6 sites of acetylene (triple bond) unsaturation. Preferred alkynyl groups include ethynyl, (—C≡CH), propargyl (or prop-1-yn-3-yl, —CH$_2$C≡CH), and the like. In the event that alkynyl is attached to nitrogen, the triple bond cannot be alpha to the nitrogen.

The term "substituted alkynyl" refers to an alkynyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NR'R", where R' and R" are independently selected from the group consisting of hydrogen, alkyl, cycloalkyl, carboxyalkyl (for example, benzyloxycarbonyl), —S(O)$_n$R, in which R is alkyl, aryl, or heteroaryl and n is 0, 1 or 2, SO$_2$NH$_2$, —C(O)NH$_2$, aryl, heteroaryl and heterocyclyl provided that R' and R" cannot both be hydrogen, or R' is a group —Y-Z, in which Y is optionally substituted alkylene and Z is alkenyl, cycloalkenyl, or alkynyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, CF$_3$, amino, substituted amino, cyano, or —S(O)$_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "non-aromatic carbocycle" as used herein refers to a 5 or 6 membered carbocyclic group consisting of carbon and hydrogen comprising 0–2 double bonds.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2. Such heteroaryl groups can have a single ring (e.g., pyridyl or furyl) or multiple condensed rings (e.g., indolizinyl, benzothiazolyl, or benzothienyl). Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

Formula V as drawn includes a "dotted line", which is defined as representing an optional double bond. This means that a double bond is either absent (and thus the compound of Formula V is a thiazoline derivative when Z is sulfur), or present (and thus the compound of Formula V is a thiazole derivative when Z is sulfur) at the 4,5-position of the 5-membered heterocyclic ring.

"Optional" or "optionally" means that the subsequently described event or circumstance may or may not occur, and that the description includes instances where said event or circumstance occurs and instances in which it does not.

The term "compound of Formula I" (or Formula II, III, IV or V) is intended to encompass the compounds of the invention as disclosed, and the pharmaceutically acceptable salts, pharmaceutically acceptable esters, and prodrugs of such compounds. Additionally, the compounds of the invention may possess one or more asymmetric centers, and can be produced as a racemic mixture or as individual enantiomers or diastereoisomers. The number of stereoisomers present in any given compound of the invention depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown can be designated (+) or (−) depending on the direction (dextro- or laevorotary) which they rotate the plane of polarized light at the wavelength of the sodium D line.

The term "therapeutically effective amount" refers to that amount of a compound of the invention that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "coronary artery disease" means a chronic disease in which there is a "hardening" (atherosclerois) of the coronary arteries.

The term "atherosclerosis" refers to a form of arteriosclerosis in which deposits of yellowish plaques containing cholesterol, lipoid material, and lipophages are formed within the intima and innner media of large and medium-sized arteries.

The term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of the invention, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Also included are amines where the two or three substituents, together with the amino nitrogen, form a heterocyclic or heteroaryl group.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Nomenclature

The compounds of the invention are named using IUPAC nomenclature, and were generated from the naming program found in ChemDraw Ultra 6.0™, ChemInovation™ Extension.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Synthesis of the Compounds of Formula I

An example of a method for preparing the compounds of Formula I is shown in Reaction Scheme I.

REACTION SCHEME I

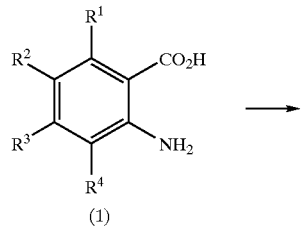

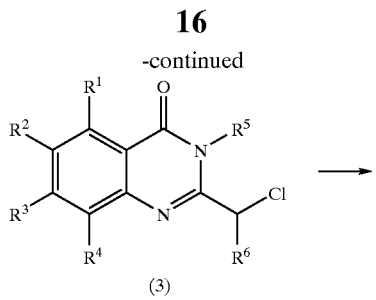

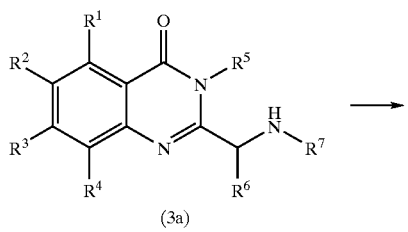

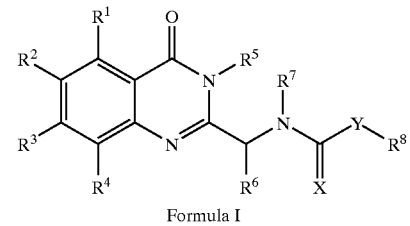

Formula I

Compounds of Formula I are either commercially available or are made by means well known in the art. For example, Reaction Scheme I shows a synthesis of the compounds of Formula I that starts from readily available 2-aminobenzoic acid derivatives of formula (1), which are reacted with appropriately substituted chloroacetyl chloride derivatives to give a compound of formula (2), which is cyclized by reaction with an amine of the formula $R^5NH_2$ to give a compound of formula (3). This in turn is reacted with compounds of formula $R^7NH_2$ to provide a compound of formula (3a), which is reacted with an acid chloride of formula $R^8$—Y—C(X)Cl, in which $R^8$, X and Y are as defined above, to provide a compound of Formula I.

REACTION SCHEME IIA

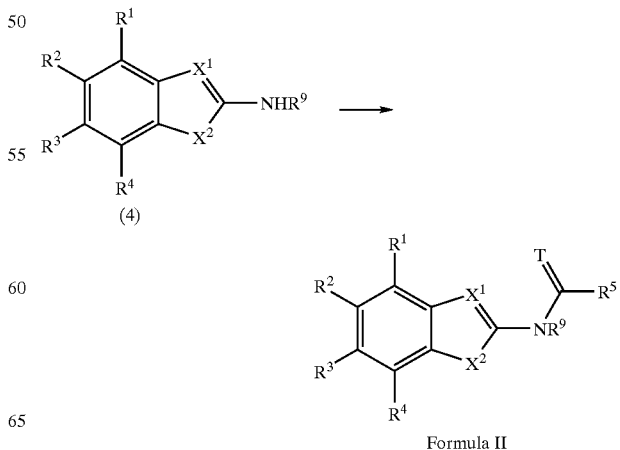

Formula II

(4) → Formula II

(4) →

Compounds of Formula II are either commercially available or are made by means well known in the art. For example, Reaction Scheme IIA shows a synthesis of the compounds of Formula II that starts from readily available optionally substituted 2-amino derivatives of formula (4), which are reacted with appropriately substituted acid chloride derivatives to give compounds of Formula II in which Y is —N($R^9$)—C(T)—. Similarly, reaction with appropriately substituted acid sulfonyl chloride derivatives provides compounds of Formula II in which Y is —N($R^9$)—$SO_2$—. Similarly, reaction with appropriately substituted isocyanates or isothiocyanates of formula $R^9$NCT provides compounds of Formula II in which Y is —N$R^9$—C(T)—N($R^9$)—.

Additionally, any Formula II amide can be converted to a thioamide by means well know to those skilled in the art, for example by treatment with Lawesson's reagent. The reaction is carried out in an inert solvent, for example chlorobenzene, at a temperature of about 80° to 120° C., for about 30 minutes to 6 hours. When the reaction is substantially complete, the thioamide of Formula II is isolated by conventional means, for example by removal of the solvent under reduced pressure, followed by chromatography of the residue on silica gel.

REACTION SCHEME IIB

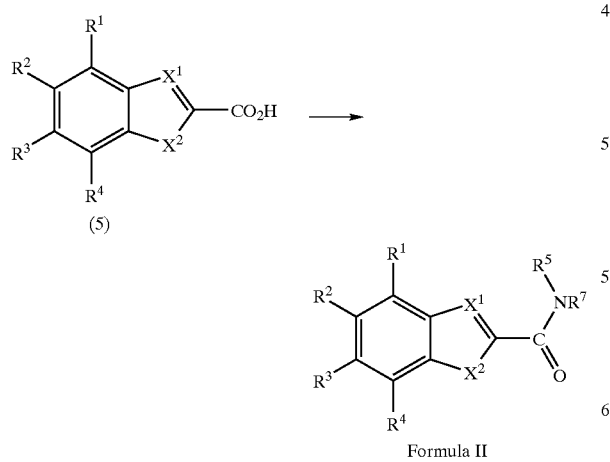

(5)

Formula II

Reaction Scheme IIB shows a synthesis of the compounds of Formula II that starts from readily available optionally substituted 2-carboxylic acid derivatives of formula (5), which are converted to an acid halide by conventional means, which is reacted with appropriately substituted amine derivatives to give compounds of Formula II in which Y is —C(O)—N($R^9$)—.

Compounds in which Y is —C(S)—N($R^9$)— may be prepared from compounds in which Y is —C(O)—N($R^9$)— by reaction with Lawesson's reagent. The reaction is carried out in an inert solvent, for example chlorobenzene, at a temperature of about 80° to 120° C., for about 30 minutes to 6 hours. When the reaction is substantially complete, the product of Formula II in which Y is —C(S)—N($R^9$)— is isolated by conventional means, for example by removal of the solvent under reduced pressure, followed by chromatography of the residue on silica gel.

REACTION SCHEME IIIA

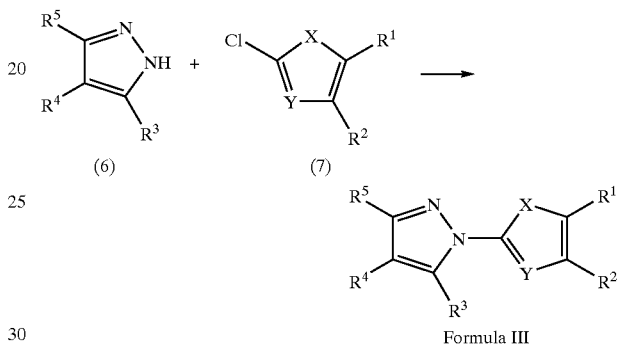

Formula III

Reaction Scheme IIIA shows a synthesis of the compounds of Formula III that starts from readily available optionally substituted pyrazole derivatives of formula (6), which are reacted with a 2-chloro-heterocycle of formula (7) conventionally, to provide compounds of Formula III. For example, compounds of formula (6) in which $R^4$ is iodo are commercially available, and the compound of Formula III with an iodo group present can be further reacted to provide various substitutions at the 4-position. Additionally, compounds of formula (6) in which $R^4$ is carboethoxy are commercially available, and the carboethoxy group can be further reacted.

Alternatively, the compound of formula (7) is reacted with hydrazine to provide the hydrazine derivative of formula (8), which in turn is reacted with an optionally substituted 1,3-propanedione derivative to give a compound of Formula III, as shown in Reaction Scheme IIIB.

REACTION SCHEME IIIb

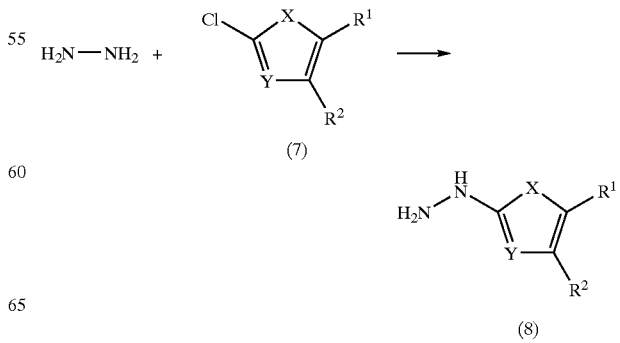

(8)

-continued (8) →

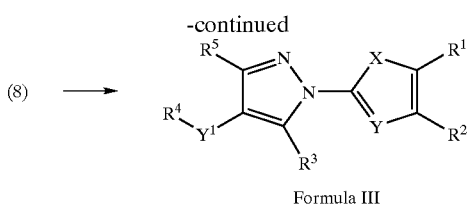

Formula III

The preparation of compounds of Formula IV is shown in Reaction Scheme IV

REACTION SCHEME IV

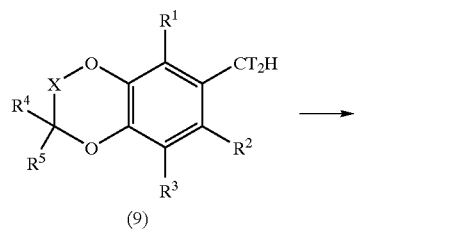

(9)

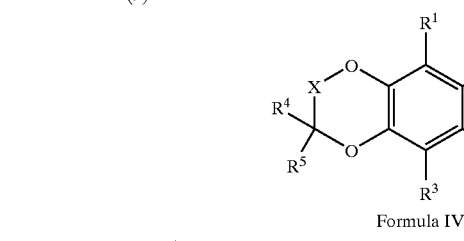

(10)

Reaction Scheme IV shows a synthesis of the compounds of Formula IV in which Y is —C(T)NHR$^6$, which starts from readily available optionally substituted derivatives of formula (10). This compound is first converted to an acid chloride by convention means (for example, thionyl chloride), which is then reacted with an amine of formula R$^6$NH$_2$ in the presence of base, to provide compounds of Formula IV where Y is —C(T)NHR$^6$.

Alternatively, the amino compound of formula (10) is reacted with an acid chloride of formula R$^6$C(T)Cl to give a compound of Formula IV in which Y is —NHC(T)R$^6$. Similarly, reaction of the compound of formula (10) with an isocyanate or isothiocyanate of formula R$^6$NCT gives a compound of Formula IV in which Y is —NHC(T)NHR$^6$, and reaction of the compound of formula (10) with a sulfonyl chloride of formula R$^6$SO$_2$Cl gives a compound of Formula IV in which Y is —NHSO$_2$R$^6$.

The preparation of compounds of Formula V is shown in Reaction Scheme IV

REACTION SCHEME V

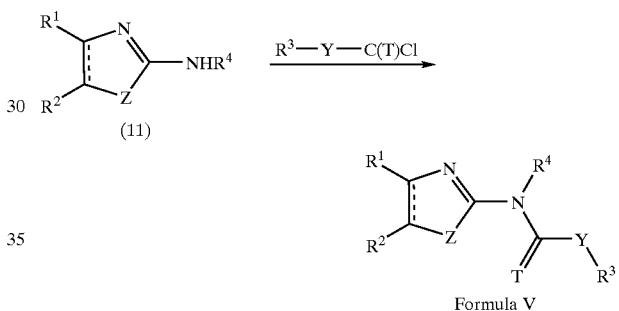

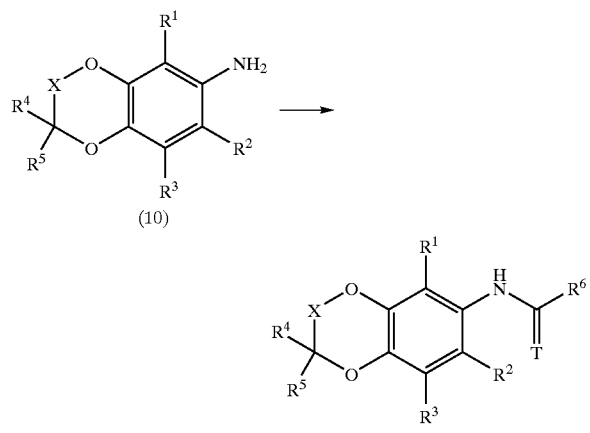

Reaction Scheme V shows a synthesis of the compounds of Formula V that starts from readily available optionally substituted 2-amino derivatives of formula (11), which are reacted with an acid chloride of formula R$^3$YC(T)Cl to provide compounds of Formula V.

Alternatively, an optionally substituted acid chloride of formula (12) is reacted with an amine of formula R$^3$YNHR$^4$ to provide compounds of Formula V.

A synthesis of compound of Formula V where the dotted line is a double bond, X is —NHC(T)—, and Z is sulfur, is shown in Reaction Scheme Va.

REACTION SCHEME Va

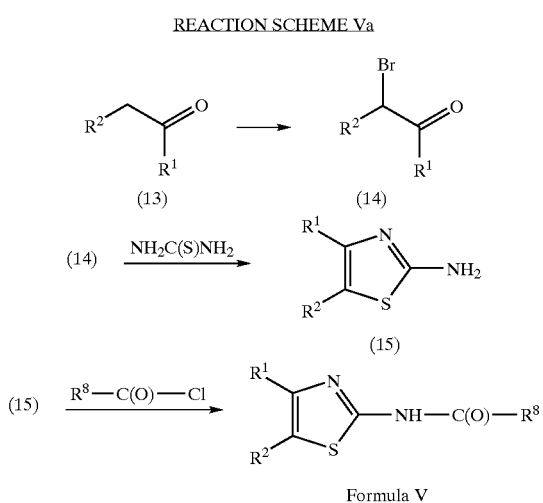

Formula V

Step 1—Preparation of (14)

Compounds of formula (13) are commercially available, or prepared by means well known in the art. The compound of formula (13) in general is dissolved in an inert solvent, for example methylene chloride, and a halogen added, preferably bromine, at a temperature of about 0° C. The reaction mixture is then heated at about 40° C. for about 30 minutes. When the reaction is substantially complete, the product of formula (14) is isolated by conventional means, for example by filtration and removal of the solvent under reduced pressure. The product is preferably used in the next step without further purification.

Step 2—Preparation of Formula (15)

The compound of formula (14) is then reacted with thiourea in an inert solvent, for example ethanol, at a temperature of about 80° C., for about 4 hours. When the reaction is substantially complete, the product of formula (15) is isolated and purified by conventional means, for example by chromatography on silica gel.

Step 3—Preparation of a Compound of Formula V

The compound of formula (15) is then reacted with an acid chloride of formula $R^8$—C(O)—Cl, in an inert solvent, for example methylene chloride, in the presence of a tertiary base, for example triethylamine. The reaction is initially conducted at about 0° C., followed by about 25C overnight. When the reaction is substantially complete, the product of Formula V is isolated and purified by conventional means, for example by HPLC.

Utility, Testing and Administration

General Utility

The compounds of the invention stimulate the expression of ABCA-1 in mammalian cells, increase cholesterol efflux and raise HDL levels in plasma. Thus, the compounds of the invention are useful for treating conditions related to high cholesterol/low HDL levels in mammals, including, but not limited to, coronary artery disease, including diabetes.

Testing

Activity testing is conducted as described in those patents and patent applications referenced above, and in the Examples below, and by methods apparent to one skilled in the art.

Pharmaceutical Compositions

The compounds of the invention are usually administered in the form of pharmaceutical compositions. This invention therefore provides pharmaceutical compositions that contain, as the active ingredient, one or more of the compounds of the invention, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of the invention may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17$^{th}$ Ed. (1985) and "Modern Pharmaceutics", Marcel Dekker, Inc. 3$^{rd}$ Ed. (G. S. Banker & C. T. Rhodes, Eds.).

Administration

The compounds of the invention may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of the invention. Administration may be via capsule or enteric coated tablets, or the like. In making the pharmaceutical compositions that include at least one compound of the invention, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of the invention are effective over a wide dosage range and is generally administered in a pharmaceutically effective amount. Preferably, for oral administration, each dosage unit contains from 10 mg to 2 g of a compound of the invention, more preferably from 10 to 700 mg, and for parenteral administration, preferably from 10 to 700 mg of a compound of the invention, more preferably about 50–200 mg. It will be understood, however, that the amount of the compound of the invention actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preferred Examples of Compounds of Formula I

The following compounds of Formula I were tested and found to elevate cellular expression of the ABCA-1 gene. The compounds are either commercially available, or are prepared by means well known in the arts.

3-(4-bromo-phenyl)-1-[1-(7-chloro-4-oxo-3-p-tolyl-3,4-dihydro-quinazolin-2-yl)-ethyl]-1-propyl-urea;

3,5,5-trimethylhexanoic acid benzyl-[1-(4-oxo-3-propyl-3,4-dihydro-quinazolin-2-yl)propyl]-amide;

1-{1-[3-(4-bromophenyl)-4-oxo-3,4-dihydro-quinazolin-2-yl]-ethyl}-3-(2-methoxy-phenyl-1-phenethylurea;

4-{1-[3-(4-ethoxyphenyl)-4-oxo-3,4-dihydro-quinazolin-2-yl]-ethyl}-piperazine-1-carboxylic acid (2,4-dimethoxy-phenyl)-amide.

N-{[3-(4-chlorophenyl)-4-oxo(3-hydroquinazolin-2-yl)]ethyl}-N-(2-furylmethyl){[4-(methylethyl)phenyl]amino}carboxamide;

N-{[3-(3,4-dimethylphenyl)-4-oxo(3-hydroquinazolin-2-yl)]propyl}[(4-chlorophenyl)amino]-N-(2-methoxyethyl)carboxamide;

[(2,6-dimethylphenyl)amino]-N-[(3-(2-naphthyl)-4-oxo(3-hydroquinazolin-2-yl))ethyl]-N-benzylcarboxamide;

N-[2-(dimethylamino)ethyl][(3-methoxyphenyl)amino]-N-[(3-(2-naphthyl)-4-oxo(3-hydroquinazolin-2-yl))ethyl] carboxamide;
ethyl 2-({N-[2-(dimethylamino)ethyl]-N-[(3-(2-naphthyl)-4-oxo(3-hydroquinazolin-2-yl))ethyl]carbamoyl}amino) acetate;
N-(2-methylpropyl)(naphthylamino)-N-[(3-(2-naphthyl)-4-oxo(3-hydroquinazolin-2-yl))ethyl]carboxamide;
[(3-chlorophenyl)amino]-N-(2-methylpropyl)-N-[(3-(2-naphthyl)-4-oxo(3-hydroquinazolin-2-yl))ethyl] carboxamide;
[(3-bromophenyl)amino]-N-(2-methylpropyl)-N-[(3-(2-naphthyl)-4-oxo(3-hydroquinazolin-2-yl))ethyl] carboxamide;
[(4-chlorophenyl)amino]-N-(2-methylpropyl)-N-[(3-(2-naphthyl)-4-oxo(3-hydroquinazolin-2-yl))ethyl] carboxamide;
[(2-methylphenyl)amino]-N-(2-methylpropyl)-N-[(3-(2-naphthyl)-4-oxo(3-hydroquinazolin-2-yl))ethyl] carboxamide;
N-(2-methylpropyl)-N-[(3-(2-naphthyl)-4-oxo(3-hydroquinazolin-2-yl))ethyl]{[3-(trifluoromethyl)phenyl]amino}carboxamide;
N-(2-methylpropyl)[(4-methylthiophenyl)amino]-N-[(3-(2-naphthyl)-4-oxo(3-hydroquinazolin-2-yl))ethyl] carboxamide;
(butylamino)-N-{[7-chloro-3-(4-methylphenyl)-4-oxo(3-hydroquinazolin-2-yl)]ethyl}-N-(3-methylbutyl) carboxamide;
N-{[7-chloro-3-(4-methylphenyl)-4-oxo(3-hydroquinazolin-2-yl)]ethyl}[(3-methoxyphenyl)amino]-N-propylcarboxamide;
N-{[3-(4-bromophenyl)-4-oxo(3-hydroquinazolin-2-yl)]ethyl}(ethylamino)-N-(2-furylmethyl)carboxamide;
N-[2-(dimethylamino)ethyl][(3-cyanophenyl)amino]-N-[(3-(2-naphthyl)-4-oxo(3-hydroquinazolin-2-yl))ethyl] carboxamide;
[(2,4-difluorophenyl)amino]-N-[2-(dimethylamino)ethyl]-N-[(3-(2-naphthyl)-4-oxo(3-hydroquinazolin-2-yl))ethyl] carboxamide;
N-{[3-(3,4-dimethylphenyl)-4-oxo(3-hydroquinazolin-2-yl)]propyl}[(4-methoxyphenyl)amino]-N-benzylcarboxamide;
[(4-methylphenyl)amino]-N-(2-methylpropyl)-N-[(3-(2-naphthyl)-4-oxo(3-hydroquinazolin-2-yl))ethyl] carboxamide;
[(4-bromophenyl)amino]-N-[(3-(2-naphthyl)-4-oxo(3-hydroquinazolin-2-yl))ethyl]-N-propylcarboxamide;
[(3-fluorophenyl)amino]-N-[(3-(2-naphthyl)-4-oxo(3-hydroquinazolin-2-yl))ethyl]-N-propylcarboxamide;
(butylamino)-N-{[7-chloro-3-(4-methylphenyl)-4-oxo(3-hydroquinazolin-2-yl)]ethyl}-N-(2-furylmethyl) carboxamide;
N-{[3-(4-bromophenyl)-4-oxo(3-hydroquinazolin-2-yl)]ethyl}-N-butyl[(4-methoxyphenyl)amino]carboxamide;
ethyl 2-[(N-{[3-(4-bromophenyl)-4-oxo(3-hydroquinazolin-2-yl)]ethyl}-N-(2-methoxyethyl)carbamoyl)amino] acetate; and
[(2,4-difluorophenyl)amino]-N-{[3-(4-chlorophenyl)-4-oxo(3-hydroquinazolin-2-yl)]propyl}-N-(2-methoxyethyl) carboxamide.

EXAMPLE 2

Preferred Examples of Compounds of Formula II

The following compounds of Formula II were tested and found to elevate cellular expression of the ABCA-1 gene.

The compounds are either commercially available, or are prepared by means well known in the arts.
N-(6-ethoxybenzothiazol-2-yl)propanamide;
N-benzothiazol-2-yl(butylamino)carboxamide;
[t-butylamino]-N-(6-ethoxybenzothiazol-2-yl)carboxamide;
N-benzothiazol-2-yl(tert-butylamino)carboxamide;
N-(6-ethoxybenzothiazol-2-yl)(phenylamino)carboxamide;
N-(2,6-dimethylphenyl)(3-chlorobenzo[b]thiophen-2-yl) carboxamide;
N-[6-(methylsulfonyl)benzothiazol-2-yl]-2-thienylcarboxamide;
2-furyl-N-[6-(methylsulfonyl)benzothiazol-2-yl] carboxamide;
benzothiazol-2-yl-(3-methoxyphenyl)amine;
N-benzothiazol-2-yl-2-[3-cyano-6-(2-thienyl)-4-(trifluoromethyl)(2-pyridylthio)]acetamide;
N-benzothiazol-2-yl(propylamino)carboxamide;
N-benzothiazol-2-yl[(3-chlorophenyl)amino]carboxamide;
N-benzothiazol-2-yl-3-cyclopentylpropanamide;
N-(2H,4H-benzo[e]1,3-dioxan-7-yl)(3-chlorobenzo[b] thiophen-2-yl)carboxamide;
(3-chlorobenzo[b]thiophen-2-yl)-N-(2-pyridyl)ethyl) carboxamide;
(5-bromo(2-furyl))-N-(3-cyanobenzo[b]thiophen-2-yl) carboxamide;
N-(2,5-dimethylphenyl)(3-chlorobenzo[b]thiophen-2-yl) carboxamide;
(3-chlorobenzo[b]thiophen-2-yl)-N-(3-methylphenyl) carboxamide;
2-[({2-[4-(6-chlorobenzothiazol-2-yl)piperazinyl] ethyl}oxycarbonyl)methylthio]acetic acid;
N-benzothiazol-2-ylpentanamide;
N-[4-(6-methylbenzothiazol-2-yl)phenyl](2-methylphenyl) carboxamide;
N-[4-(6-methylbenzothiazol-2-yl)phenyl]-2-(2-thienyl) acetamide;
2-furyl-N-[4-(6-methylbenzothiazol-2-yl)phenyl] carboxamide;
(3-chlorobenzo[b]thiophen-2-yl)-N-(ethynylcyclohexyl) carboxamide;
benzo[b]thiophen-2-yl-N-(2,4-difluorophenyl)carboxamide;
(3-chlorobenzo[b]thiophen-2-yl)-N-(4-chlorophenyl) carboxamide;
(3-chlorobenzo[b]thiophen-2-yl)-N-(4-bromophenyl) carboxamide;
(3-chlorobenzo[b]thiophen-2-yl)-N-(2-naphthyl) carboxamide;
(2-{ethyl[3-(N-ethyl-3-furylcarbonylamino)propyl] amino}benzoxazol-5-yl)-N-(4-methoxyphenyl) carboxamide;
[2-(ethyl{3-[N-ethyl(3-fluoro-2-methylphenyl) carbonylamino]propyl}amino)benzoxazol-5-yl]-N-(4-methoxyphenyl)carboxamide;
N-[2-(2-fluorophenyl)ethyl][2-(4-{2-[4-(trifluoromethyl) phenyl]acetyl}(1,4-diazaperhydroepinyl))benzoxazol-5-yl]carboxamide;
N-[2-(2-fluorophenyl)ethyl]{2-[4-(3-indol-3-ylpropanoyl) (1,4-diazaperhydroepinyl)]benzoxazol-5-yl}carboxamide;
1-{5-[(1E)-1-aza-2-(3-nitrophenyl)vinyl]benzoxazol-2-yl}-4-methoxybenzene;
N-[4-(5,7-dimethylbenzoxazol-2-yl)phenyl](2-bromophenyl)carboxamide; and
(2E)-3-(2-furyl)-2-(5-methylbenzimidazol-2-yl)prop-2-enenitrile.

EXAMPLE 3

Preferred Examples of Compounds of Formula III

The following compound of Formula III was tested and found to elevate cellular expression of the ABCA-1 gene.

The compound is commercially available, or may be prepared by means well known in the arts.

N-[4-(diethylamino)-1-methylbutyl]{1-[4-(3-methoxyphenyl)(1,3-thiazol-2-yl)]-5-methylpyrazol-4-yl}carboxamide;

N-[4-(diethylamino)-1-methylbutyl]{1-[4-(4-bromophenyl)(1,3-thiazol-2-yl)]-5-ethylpyrazol-4-yl}carboxamide;

N-(2,2-dimethyl-4-phenyl(1,3-dioxan-5-yl)){5-ethyl-1-[4-(4-methylphenyl)(1,3-thiazol-2-yl)]pyrazol-4-yl}carboxamide;

N-bicyclo[2.2.1]hept-2-yl {5-methyl-1-[4-(4-methylphenyl)(1,3-thiazol-2-yl)]pyrazol-4-yl}carboxamide;

N-adamantanyl {5-ethyl-1-[4-(4-methylphenyl)(1,3-thiazol-2-yl)]pyrazol-4-yl}carboxamide;

{5-ethyl-1-[4-(4-methylphenyl)(1,3-thiazol-2-yl)]pyrazol-4-yl}-N-(2-phenylethyl)carboxamide;

{5-methyl-1-[4-(4-fluorophenyl)(1,3-thiazol-2-yl)]pyrazol-4-yl}-N-(2-phenylethyl)carboxamide;

{1-[4-(tert-butyl)(1,3-thiazol-2-yl)]-5-methylpyrazol-4-yl}-N-cyclopropylcarboxamide;

{1-[4-(4-bromophenyl)(1,3-thiazol-2-yl)]-5-ethylpyrazol-4-yl}-N-hexylcarboxamide;

{1-[4-(4-bromophenyl)(1,3-thiazol-2-yl)]-5-ethylpyrazol-4-yl}-N-(2-methylpropyl)carboxamide;

N-cyclopropyl[5-methyl-1-(4-phenyl(1,3-thiazol-2-yl))pyrazol-4-yl]carboxamide;

{5-methyl-1-[4-(4-methylphenyl)(1,3-thiazol-2-yl)]pyrazol-4-yl}-N-pentylcarboxamide;

{5-methyl-1-[4-(4-methylphenyl)(1,3-thiazol-2-yl)]pyrazol-4-yl}-N-butylcarboxamide;

{5-ethyl-1-[4-(4-methoxyphenyl)(1,3-thiazol-2-yl)]pyrazol-4-yl}-N-(3-methylbutyl)carboxamide;

N-(1,2-dimethylpropyl){5-ethyl-1-[4-(4-methylphenyl)(1,3-thiazol-2-yl)]pyrazol-4-yl}carboxamide;

{1-[4-(3-methoxyphenyl)(1,3-thiazol-2-yl)]-5-methylpyrazol-4-yl}-N-(methylethyl)carboxamide; and {1-[4-(4-chlorophenyl)(1,3-thiazol-2-yl)]-5-methylpyrazol-4-yl}-N-benzylcarboxamide.

1-(4-{1-[4-(3-methoxy-phenyl)-thiazol-2-yl]-5-propyl-1H-pyrazole-4-carbonyl}-2-methyl-piperazin-1-yl)-2-phenyl-butan-1-one;

1-(4-{5-ethyl-1-[4-(4-methoxy-phenyl)-thiazol-2-yl]-1H-pyrazole-4-carbonyl}-2-methyl-piprazin-1-yl)-2,2-diphenyl-ethanone;

1-(4-{1-[4-(4-chloro-phenyl)-thiazol-2-yl]-5-ethyl-1H-pyrazole-4-carbonyl}-2-methyl-piperazin-1-yl)-2,2-diphenyl-ethanone;

1-(4-{1-[4-(4-chloro-phenyl)-thiazol-2-yl]-5-ethyl-1H-pyrazole-4-carbonyl}-2-methyl-piperazin-1-yl)-2-phenyl-butan-1-one;

{1-[4-(4-chloro-phenyl)-thiazol-2-yl]-5-ethyl-1H-pyrazol-4-yl}-[3-methyl-4-(naphthalene-2-carbonyl)-piperazin-1-yl]-methanone;

[4-(3-bromo-benzoyl)-3-methyl-piperazin-1-yl]-{1-[4-(4-chloro-phenyl)-thiazol-2-yl]-5-ethyl-1H-pyrazol-4-yl}-methanone;

5-isopropyl-1-(4-p-tolyl-thiazol-2-yl)-1H-pyrazole-4-carboxylic acid (3-methyl-butyl)-amide;

1-(4-{5-ethyl-1-[4-(4-methoxy-phenyl)-thiazol-2-yl]-1H-pyrazole-4-carbonyl}-2-metyl-piperazin-1-yl)-2-methyl-propan-1-one;

[4-(biphenyl-4-carbonyl)-3-methyl-piperazin-1-yl]-{5-ethyl-1-[4-(4-methoxy-phenyl)-thiazol-2-yl]-1H-pyrazol-4-yl}-methanone;

5-isopropyl-1-(4-p-tolyl-thiazol-2-yl)-1H-pyrazole-4-carboxylic acid cyclopropylamide;

5-isopropyl-1-(4-p-tolyl-thiazol-2-yl)-1H-pyrazole-4-carboxylic acid (1-phenyl-ethyl)-amide;

5-ethyl-1-[4-(4-methoxy-phenyl)-thiazol-2-yl]-1H-pyrazole-4-carboxylic acid (furan-2-ylmethyl)-amide;

5-ethyl-1-(4-p-tolyl-thiazol-2-yl)-1H-pyrazole-4-carboxylic acid (furan-2-ylmethyl)-amide; and 5-methyl-1-(4-p-tolyl-thiazol-2-yl)-1H-pyrazole-4-carboxylic acid phenethyl-amide.

EXAMPLE 4

Preferred Examples of Compounds of Formula IV

The following compounds of Formula IV were tested and found to elevate cellular expression of the ABCA-1 gene. The compounds are either commercially available, or are prepared by means well known in the arts.

N-(2H,3H-benzo[e]1,4-dioxan-6-yl)(2-chloro-4-nitrophenyl)carboxamide;

(2H,3H-benzo[e]1,4-dioxin-6-ylamino)-N-cyclohexylcarboxamide;

(2H,3H-benzo[e]1,4-dioxin-6-ylamino)-N-(3-chlorophenyl)carboxamide;

N-(2H,3H-benzo[e]1,4-dioxan-6-yl)[4-(tert-butyl)phenyl]carboxamide;

N-(2H,3H-benzo[e]1,4-dioxin-6-yl)-2-(phenylmethoxy)acetamide;

N-(2H,3H-benzo[e]1,4-dioxin-6-yl)-3-cyclopentylpropanamide;

N-(2H,3H-benzo[e]1,4-dioxin-6-yl)[(3,4-dichlorophenyl)amino]carboxamide;

N-(2H,3H-benzo[e]1,4-dioxin-6-yl)[cyclohexylamino]carboxamide;

N-(2H,3H-benzo[e]1,4-dioxin-6-yl)[(3-chlorophenyl)amino]carboxamide;

N-(2H,3H-benzo[e]1,4-dioxin-6-yl)[(2-chloro-4-nitrophenyl)amino]carboxamide;

N-(2H,3H-benzo[e]1,4-dioxin-6-yl)[(2-bromophenyl)amino]carboxamide;

N-(2H,3H-benzo[e]1,4-dioxin-6-yl)[4-(tert-butyl)phenyl]carboxamide;

methyl 4-{(1E)-1-aza-2-[4-(2H-benzo[d]1,3-dioxolen-5-ylmethyl)piperazinyl]-2-(cyclohexylamino)vinyl}-3-hydroxybenzoate;

ethyl 1-(2H-benzo[d]1,3-dioxolen-5-ylcarbonyl)piperidine-2-carboxylate;

ethyl 3-[2H-benzo[d]1,3-dioxolen-5-yl-N-(2-phenylethyl)carbonylamino]propanoate;

2H-benzo[d]1,3-dioxolen-5-yl-N-[(9-ethylcarbazol-3-yl)methyl]-N-(2-phenylethyl)carboxamide;

N-(2H,3H-benzo[e]1,4-dioxin-6-yl)-3-cyclopentylpropanamide;

N-(2H,3H-benzo[e]1,4-dioxin-6-yl)[(3,4-dichlorophenyl)amino]carboxamide;

N-(2H,3H-benzo[e]1,4-dioxin-6-yl)[cyclohexylamino]carboxamide;

N-(2H,3H-benzo[e]1,4-dioxin-6-yl)[(3-chlorophenyl)amino]carboxamide;

N-(2H,3H-benzo[e]1,4-dioxin-6-yl)[(2-chloro-4-nitrophenyl)amino]carboxamide;

N-(2H,3H-benzo[e]1,4-dioxin-6-yl)[(2-bromophenyl)amino]carboxamide; and

N-(2H,3H-benzo[e]1,4-dioxin-6-yl)[4-(tert-butyl)phenyl]carboxamide.

EXAMPLE 5

Preferred Examples of Compounds of Formula V

A. 2-Aminothiazole (38 mg, 0.37 mmole) was dissolved in dry tetrahydrofuran (6.5 ml) followed by addition of triethylamine (77 mg, 0.76 mmole) and 4-t-butylbenzoyl chloride (151 mg, 0.76 mmole). The reaction was stirred overnight at room temperature, and then the solvent removed under reduced pressure. The residue was purified by reverse phase HPLC (water/acetonitrile gradient), giving [4-(tert-butyl)phenyl]-N-(1,3-thiazolin-2-yl)carboxamide. The product was characterized by HPLC-MS.

Alternative Preparation of Compounds of Formula V Preparation of a Compound of Formula V in which $R^1$ is Phenyl, $R^2$ is Hydrogen, $R^3$ is Cyclopropyl, X is —NH—C(O)—, Y is a Covalent Bond, and the Dotted Line is a Double Bond

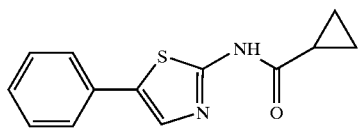

A. To a stirred solution of phenylacetaldehyde (2.92 mL, 25 mmol) in methylene chloride (15 mL) was added bromine (1.28 mL, 25 mmol) in methylene chloride (10 mL) at 0° C. dropwise. The resulting mixture was refluxed for 30 minutes, then cooled and washed with 10% aqueous sodium bicarbonate (3×20 mL). The organic layer was dried over sodium sulfate, and the filtrate evaporated under reduced pressure. The residue (2-bromophenylacetaldehyde) was used directly in the next step.

B. The 2-bromophenylacetaldehyde obtained from the previous step and thiourea (3.81 g, 50 mmol) were refluxed in ethanol (45 mL) for 2 hours. The solvent was removed and the residue was dissolved in ethyl acetate (60 mL) and washed with 10% aqueous $NaHCO_3$ (3×40 mL). The organic layer was dried over $Na_2SO_4$, and the filtrate evaporated under reduced pressure. Column chromatography (Ethyl Acetate:Hexanes=3:2) of the residue gave 5-phenyl-1,3-thiazole-2-ylamine (2.7 g).

C. To a stirred solution of 5-phenyl-1,3-thiazole-2-ylamine (40 mg, 0.225 mmol) in methylene chloride (5 mL) was added cyclopropanecarbonyl chloride (14 mL, 0.15 mmol) at 0° C., followed by triethylamine (42 mL, 0.3 mmol). The resulting mixture was stirred at room temperature overnight, and purified by HPLC, to provide. cyclopropyl-N-(5-phenyl(1,3-thiazol-2-yl))carboxamide, a compound of Formula V.

D. The following compounds of Formula V were tested and found to elevate cellular expression of the ABCA-1 gene. The compounds are either commercially available, or are prepared by methods similar to those disclosed above, or by means well known in the arts.

[4-(tert-butyl)phenyl]-N-(1,3-thiazolin-2-yl)carboxamide;
[(4-pentylphenyl)amino]-N-(1,3-thiazolin-2-yl)carboxamide;
N-(1,3-thiazolin-2-yl)[4-(trifluoromethyl)phenyl]carboxamide;
N-(1,3-thiazol-2-yl)[4-(trifluoromethoxy)phenyl]carboxamide;
(4-methoxyphenyl)-N-(1,3-thiazolin-2-yl)carboxamide;
(4-chlorophenyl)-N-(1,3-thiazolin-2-yl)carboxamide;
[4-(methylethyl)phenyl]-N-(1,3-thiazolin-2-yl)carboxamide;
(3,4-dichlorophenyl)-N-(1,3-thiazolin-2-yl)carboxamide;
(3,4,5-trimethoxyphenyl)-N-(1,3-thiazolin-2-yl)carboxamide;
(4-cyanophenyl)-N-(1,3-thiazolin-2-yl)carboxamide;
(3,4-difluorophenyl)-N-(1,3-thiazolin-2-yl)carboxamide;
2H-benzo[3,4-d]1,3-dioxolan-5-yl-N-(1,3-thiazolin-2-yl)carboxamide;
(2-fluorophenyl)-N-(1,3-thiazolin-2-yl)carboxamide;
(4-fluorophenyl)-N-(1,3-thiazolin-2-yl)carboxamide;
(4-methylphenyl)-N-(1,3-thiazolin-2-yl)carboxamide;
2-{[4-(tert-butyl)phenyl]carbonylamino}-1,3-thiazoline-4-carboxylic acid;
[4-(dimethylamino)phenyl]-N-(1,3-thiazolin-2-yl)carboxamide;
(3-methoxyphenyl)-N-(1,3-thiazolin-2-yl)carboxamide;
(3,5-bistrifluoromethylphenyl)-N-(1,3-thiazolin-2-yl)carboxamide;
(3-chlorophenyl)-N-(1,3-thiazolin-2-yl)carboxamide;
(2,4-dichlorophenyl)-N-(1,3-thiazolin-2-yl)carboxamide;
methyl 4-(N-(1,3-thiazolin-2-yl)carbamoyl)benzoate;
phenyl-N-(1,3-thiazolin-2-yl)carboxamide;
(3,5-dimethoxyphenyl)-N-(1,3-thiazolin-2-yl)carboxamide;
(3-fluorophenyl)-N-(1,3-thiazolin-2-yl)carboxamide;
4-trifluoromethylphenyl-N-(1,3-thiazol-2-yl)carboxamide;
4-trifluoromethoxyphenyl-N-(1,3-thiazol-2-yl)carboxamide;
2-trifluoromethylphenyl-N-(1,3-thiazol-2-yl)carboxamide;
methyl 4-[N-(4-oxo-1,3-thiazolin-2-yl)carbamoyl]benzoate;
[4-(tert-butyl)phenyl]-N-(4-oxo(1,3-thiazolin-2-yl))carboxamide;
(4-trifluoromethoxyphenyl)-N-(4-oxo(1,3-thiazolin-2-yl))carboxamide;
(4-chlorophenyl)-N-(4-oxo(1,3-thiazolin-2-yl))carboxamide;
(2-trifluoromethylphenyl)-N-(4-oxo(1,3-thiazolin-2-yl))carboxamide;
[4-(methylethyl)phenyl]-N-(4-oxo(1,3-thiazolin-2-yl))carboxamide;
(3,4,5-trimethoxyphenyl)-N-(4-oxo(1,3-thiazolin-2-yl))carboxamide;
(4-cyanophenyl)-N-(4-oxo(1,3-thiazolin-2-yl))carboxamide;
(3,4-difluorophenyl)-N-(4-oxo(1,3-thiazolin-2-yl))carboxamide;
(4-fluorophenyl)-N-(4-oxo(1,3-thiazolin-2-yl))carboxamide;
(4-methylphenyl)-N-(4-oxo(1,3-thiazolin-2-yl))carboxamide;
[4-(dimethylamino)phenyl]-N-(4-oxo(1,3-thiazolin-2-yl))carboxamide;
(3-methoxyphenyl)-N-(4-oxo(1,3-thiazolin-2-yl))carboxamide;
(3-chlorophenyl)-N-(4-oxo(1,3-thiazolin-2-yl))carboxamide;
(3,4-dichlorophenyl)-N-(4-oxo(1,3-thiazolin-2-yl))carboxamide;
phenyl-N-(4-oxo(1,3-thiazolin-2-yl))carboxamide;
(3,5-dimethoxyphenyl)-N-(4-oxo(1,3-thiazolin-2-yl))carboxamide;
(3-fluorophenyl)-N-(4-oxo(1,3-thiazolin-2-yl))carboxamide;
2-[(4-methoxyphenyl)carbonylamino]-1,3-thiazoline-4-carboxylic acid;
2-[(4-methylethylphenyl)carbonylamino]-1,3-thiazoline-4-carboxylic acid;
2-[(2-trifluoromethylphenyl)carbonylamino]-1,3-thiazoline-4-carboxylic acid;
2-[(3,4-dichlorophenyl)carbonylamino]-1,3-thiazoline-4-carboxylic acid;
2-[(3,4,5-trimethoxyphenyl)carbonylamino]-1,3-thiazoline-4-carboxylic acid;

2-(2H-benzo[3,4-d]1,3-dioxolan-5-ylcarbonylamino)-1,3-thiazoline-4-carboxylic acid;
2-[(4-methylphenyl)carbonylamino]-1,3-thiazoline-4-carboxylic acid;
2-[(3-methoxyphenyl)carbonylamino]-1,3-thiazoline-4-carboxylic acid; and
2-[(3,5-bistrifluoromethylphenyl)carbonylamino]-1,3-thiazoline-4-carboxylic acid;
N-[6-(methylsulfonyl)benzothiazol-2-yl]-2-thienylcarboxamide;
(2,4-difluorophenyl)-N-(4-(2-naphthyl)(1,3-thiazol-2-yl))carboxamide;
N-(4-(2-naphthyl)(1,3-thiazol-2-yl))[4-(trifluoromethoxy)phenyl]carboxamide;
cyclopentyl-N-(4-(2-naphthyl)(1,3-thiazol-2-yl))carboxamide;
N-(4-naphthyl(1,3-thiazol-2-yl))(4-phenylphenyl)carboxamide;
N-(4-naphthyl(1,3-thiazol-2-yl))[4-(trifluoromethoxy)phenyl]carboxamide;
N-(4-naphthyl(1,3-thiazol-2-yl))[3-(trifluoromethyl)phenyl]carboxamide;
(4-cyanophenyl)-N-(4-(2-naphthyl)(1,3-thiazol-2-yl))carboxamide;
[4-(tert-butyl)phenyl]-N-(4-(2-naphthyl)(1,3-thiazol-2-yl))carboxamide;
[4-(tert-butyl)phenyl]-N-(4-naphthyl(1,3-thiazol-2-yl))carboxamide;
(2,4-difluorophenyl)-N-(4-naphthyl(1,3-thiazol-2-yl))carboxamide;
N-(4-(2-naphthyl)(1,3-thiazol-2-yl))[3-(trifluoromethyl)phenyl]carboxamide;
N-(5-phenyl(1,3-thiazol-2-yl))[3-(trifluoromethyl)phenyl]carboxamide;
(2,4-difluorophenyl)-N-(5-phenyl(1,3-thiazol-2-yl)) carboxamide;
[2-fluoro-4-(trifluoromethyl)phenyl]-N-(5-phenyl(1,3-thiazol-2-yl))carboxamide;
[3-fluoro-4-(trifluoromethyl)phenyl]-N-(5-phenyl(1,3-thiazol-2-yl))carboxamide;
N-(5-phenyl(1,3-thiazol-2-yl))[4-(trifluoromethoxy)phenyl]carboxamide;
(4-cyanophenyl)-N-(5-phenyl(1,3-thiazol-2-yl))carboxamide;
cyclopentyl-N-(5-phenyl(1,3-thiazol-2-yl))carboxamide;
(2,4-difluorophenyl)-N-[4-(4-chlorophenyl)(1,3-thiazol-2-yl)]carboxamide;
N-[4-(4-chlorophenyl)(1,3-thiazol-2-yl)][3-(trifluoromethyl)phenyl]carboxamide;
[4-(tert-butyl)phenyl]-N-[4-(4-chlorophenyl)(1,3-thiazol-2-yl)]carboxamide;
N-[4-(4-chlorophenyl)(1,3-thiazol-2-yl)](4-phenylphenyl)carboxamide;
N-[4-(4-chlorophenyl)(1,3-thiazol-2-yl)][2-fluoro-4-(trifluoromethyl)phenyl]-carboxamide;
N-[4-(4-chlorophenyl)(1,3-thiazol-2-yl)][4-(trifluoromethoxy)phenyl]carboxamide;
N-[4-(4-chlorophenyl)(1,3-thiazol-2-yl)] cyclopentylcarboxamide;
N-benzothiazol-2-yl(4-cyanophenyl)carboxamide;
[4-(tert-butyl)phenyl]-N-(5-phenyl(1,3-thiazol-2-yl))carboxamide;
2-methyl-3-[(4-(2-naphthyl)(1,3-thiazol-2-yl))amino]benzoic acid;
N-benzothiazol-2-yl[3-(2-chlorophenyl)-5-methylisoxazol-4-yl]carboxamide;
2-naphthyl-N-(5-phenyl(1,3-thiazol-2-yl))carboxamide;
[3-(2-chlorophenyl)-5-methylisoxazol-4-yl]-N-(5-phenyl(1,3-thiazol-2-yl))carboxamide;
isoxazol-5-yl-N-(5-phenyl(1,3-thiazol-2-yl))carboxamide;
(2,5-dimethyl(3-furyl))—N-(5-phenyl(1,3-thiazol-2-yl))carboxamide;
N-(5-phenyl(1,3-thiazol-2-yl))-2-(2-thienyl)acetamide;
N-(5-phenyl(1,3-thiazol-2-yl))-2-pyridylcarboxamide;
cyclohexyl-N-(5-phenyl(1,3-thiazol-2-yl))carboxamide;
cyclopropyl-N-(5-phenyl(1,3-thiazol-2-yl))carboxamide;
(4-methoxyphenyl)-N-(4-phenyl(1,3-thiazol-2-yl))carboxamide;
(4-cyanophenyl)-N-(4-phenyl(1,3-thiazol-2-yl))carboxamide;
(3,4-dimethylphenyl)-N-(4-phenyl(1,3-thiazol-2-yl))carboxamide;
N-benzothiazol-2-yl-4-pyridylcarboxamide;
N-benzothiazol-2-yl-2-pyridylcarboxamide;
N-benzothiazol-2-yl-2-furylcarboxamide;
N-benzothiazol-2-yl-2-thienylcarboxamide;
N-benzothiazol-2-yl-2-(2-thienyl)acetamide;
N-benzothiazol-2-ylisoxazol-5-ylcarboxamide;
N-(4-chlorobenzothiazol-2-yl)(4-cyanophenyl)carboxamide;
N-benzothiazol-2-yl[3,5-bis(trifluoromethyl)phenyl]carboxamide;
N-benzothiazol-2-yl(3-chlorobenzo[b]thiophen-2-yl)carboxamide;
benzo[b]thiophen-2-yl-N-benzothiazol-2-ylcarboxamide;
N-benzothiazol-2-yl[3-(6-chloro-2-fluorophenyl)-5-methylisoxazol-4-yl]carboxamide;
N-benzothiazol-2-yl[1-(4-chlorophenyl)-5-(trifluoromethyl)pyrazol-4-yl]carboxamide;
N-benzothiazol-2-yl[1-phenyl-5-(trifluoromethyl)pyrazol-4-yl]carboxamide;
N-benzothiazol-2-ylcyclobutylcarboxamide;
N-benzothiazol-2-yl[1-(4-chlorophenyl)-5-propylpyrazol-4-yl]carboxamide;
N-benzothiazol-2-yl(3-fluorophenyl)carboxamide;
N-benzothiazol-2-yl(3-cyanophenyl)carboxamide;
N-(4-chlorobenzothiazol-2-yl)(3-cyanophenyl)carboxamide;
N-(6-chlorobenzothiazol-2-yl)(3-cyanophenyl)carboxamide;
(4-chlorophenyl)-N-[5-(4-methylphenyl)(1,3-thiazol-2-yl)]carboxamide;
cyclopropyl-N-[5-(4-fluorophenyl)(1,3-thiazol-2-yl)]carboxamide;
N-[5-(4-fluorophenyl)(1,3-thiazol-2-yl)]-2-thienylcarboxamide;
N-[5-(4-fluorophenyl)(1,3-thiazol-2-yl)]-2-furylcarboxamide;
N-[5-(2-chlorophenyl)(1,3-thiazol-2-yl)] cyclopropylcarboxamide;
N-(4-chlorobenzothiazol-2-yl)-2-furylcarboxamide;
N-(4-chlorobenzothiazol-2-yl)-2-thienylcarboxamide;
(2,2-difluorobenzo[3,4-d]1,3-dioxolen-5-yl)-N-(4-chlorobenzothiazol-2-yl)carboxamide;
N-(4-chlorobenzothiazol-2-yl)[1-(4-chlorophenyl)-5-propylpyrazol-4-yl]carboxamide;
N-(4-chlorobenzothiazol-2-yl)(3-fluorophenyl)carboxamide;
benzo[b]thiophen-2-yl-N-(4-chlorobenzothiazol-2-yl)carboxamide;
N-[5-(2-chlorophenyl)(1,3-thiazol-2-yl)]-2-furylcarboxamide; and
N-benzothiazol-2-yl[1-benzylpyrazol-4-yl]carboxamide.

EXAMPLE 6

Examples of Other Compounds

The following compounds were tested and found to elevate cellular expression of the ABCA-1 gene. The compounds are either commercially available, or are prepared by means well known in the arts.

(2-chloro-4-nitrophenyl)-N-(2-(2-pyridyl)ethyl) carboxamide;
N-(5,7-dimethylpyridino[3,2-e]pyridin-2-yl)(4-chlorophenyl)carboxamide;
2-naphthyl-N-(2-phenylethyl)carboxamide;
(4-chlorophenyl)-N-[(1-methylpyrrol-2-yl)methyl]-N-(2-(2-pyridyl)ethyl)carboxamide;
N-(2-methoxydibenzo[b,d]furan-3-yl)-2,2-dimethylpropanamide;
1-(8-aza-1,4-dioxaspiro[4.5]dec-8-yl)octan-1-one;
N-((1E)-2-phenylvinyl)-N-(4-ethylphenyl)dodecanamide;
[((2E)-2-pentyl-3-phenylprop-2-enyl)({1-[(4-butylphenyl)carbonyl](4-piperidyl)}methyl)amino]-N-benzamide;
(2E)-3-phenyl-N-[2-(phenyl{N-[3-(trifluoromethyl)phenyl]carbamoyl}amino)ethyl]prop-2-enamide;
[4-(tert-butyl)phenyl]-N-[(2-nitrophenyl)methyl]-N-(2-(2-pyridyl)ethyl)carboxamide;
ethyl 1-[(2-chloro-4-nitrophenyl)carbonyl]-4-[(2-phenylethyl)amino]-1,2,5,6-tetrahydropyridine-3-carboxylate;
ethyl 1-[(4-nitrophenyl)carbonyl]-4-[(2-phenylethyl)amino]-1,2,5,6-tetrahydropyridine-3-carboxylate;
ethyl 1-[(2,4-dichlorophenyl)carbonyl]-4-[(2-phenylethyl)amino]-1,2,5,6-tetrahydropyridine-3-carboxylate;
ethyl 1-[(2-methylphenyl)carbonyl]-4-[(2-phenylethyl)amino]-1,2,5,6-tetrahydropyridine-3-carboxylate;
ethyl 1-[(4-ethylphenyl)carbonyl]-4-[(2-phenylethyl)amino]-1,2,5,6-tetrahydropyridine-3-carboxylate;
ethyl 1-[(4-methylphenyl)carbonyl]-4-[(2-phenylethyl)amino]-1,2,5,6-tetrahydropyridine-3-carboxylate;
ethyl 1-[(4-fluorophenyl)carbonyl]-4-[(2-phenylethyl)amino]-1,2,5,6-tetrahydropyridine-3-carboxylate;
ethyl 1-[(4-methoxyphenyl)carbonyl]-4-[(2-phenylethyl)amino]-1,2,5,6-tetrahydropyridine-3-carboxylate;
ethyl 1-[(4-t-butylphenyl)carbonyl]-4-[(2-phenylethyl)amino]-1,2,5,6-tetrahydropyridine-3-carboxylate;
ethyl 1-[(4-bromophenyl)carbonyl]-4-[(2-phenylethyl)amino]-1,2,5,6-tetrahydropyridine-3-carboxylate;
ethyl 4-[(2-phenylethyl)amino]-1-[(4-phenylphenyl)carbonyl]-1,2,5,6-tetrahydropyridine-3-carboxylate;
({[4-(dimethylamino)phenyl]methyl}indan-5-ylamino)-N-(2-fluorophenyl)carboxamide;
(4-ethylphenyl)-N-(2-{[N-(4-nitrophenyl)carbamoyl]phenylamino}ethyl)carboxamide;
(4-ethylphenyl)-N-(2-{phenyl[N-(4-phenoxyphenyl)carbamoyl]amino}ethyl) carboxamide;
N-(2,3-dichlorophenyl)[butyl(2-oxo-2-(2-1,2,3,4-tetrahydroisoquinolyl)ethyl)amino]carboxamide;
1-(3-chlorophenyl)-3-ethylpyrazol-5-yl furan-2-carboxylate;
5-(2,4-dichlorophenyl)-1-[benzylsulfonyl]-3-propoxy-1,2,4-triazole;
ethyl 3-[(4-ethylphenyl)-N-(2-phenylethyl)carbonylamino]propanoate ethyl 3-[(2,4-dichlorophenyl)-N-(2-phenylethyl)carbonylamino]propanoate;
ethyl 3-[(4-chlorophenyl)-N-(2-phenylethyl)carbonylamino]propanoate;
ethyl 3-[(4-methylphenyl)-N-(2-phenylethyl)carbonylamino]propanoate;
ethyl 3-[(4-bromophenyl)-N-(2-phenylethyl)carbonylamino]propanoate;
ethyl 3-[(4-methoxyphenyl)-N-(2-phenylethyl)carbonylamino]propanoate;
N-((2E)-3-phenylprop-2-enyl)-N-(4-bromophenyl)(4-ethylphenyl)carboxamide;
N-(9-anthrylmethyl)(4-methoxyphenyl)-N-(2-phenylethyl)carboxamide;
N-(9-anthrylmethyl)(4-ethoxyphenyl)-N-{[(2-fluorophenyl)amino]carbonyl}-carboxamide;
ethyl 2-(2-{[(2-fluorophenyl)amino]carbonylamino}-1,3-thiazol-4-yl)acetate;
N-butyl[(4-thiomethylphenyl)amino]-N-{[4-(phenylmethoxy)phenyl]methyl}-carboxamide;
N-(4-methylphenyl)(4-(1,3-thiazolin-2-yl)phenoxy)carboxamide;
N-(9-ethylcarbazol-3-yl)(4-methoxyphenyl)carboxamide;
N-(9-ethylcarbazol-3-yl)(4-methylphenyl)carboxamide;
N-(9-ethylcarbazol-3-yl)(4-fluorophenyl)carboxamide;
(1E)-2-amino-1-aza-2-(3-pyridyl)vinyl 4-methoxybenzoate;
N-(9-anthrylmethyl)(4-bromophenyl)-N-(2-phenylethyl)carboxamide;
N-(2-phenylcyclopropyl)piperidylcarboxamide;
N-(2-chlorophenyl)[(3-chlorophenyl)amino]carboxamide;
N-(4-acetylphenyl)[(3-chlorophenyl)amino]carboxamide;
2-{[N-(4-chlorophenyl)carbamoyl]amino}benzoic acid;
2-[(1E)-2-(3,4-dimethoxyphenyl)vinyl]-3-hydroquinazolin-4-one;
2-{[N-(3-chlorophenyl)carbamoyl]amino}benzoic acid;
N-(2-fluorophenyl)[(3-chlorophenyl)amino]carboxamide;
N-(3,4-dichlorophenyl)[(cyclohexylmethyl)amino]carboxamide;
N-(3,4-dichlorophenyl)[(3-hydroxyphenyl)amino]carboxamide;
[(4-acetylphenyl)amino]-N-(3,4-dichlorophenyl)carboxamide;
(4-bromophenyl)-N-(2-phenylethyl)-N-{[4-(trifluoromethyl)phenyl]methyl}-carboxamide;
N-(3-methylphenyl)(2-oxochromen-3-yl)carboxamide;
(azaindanylidenemethoxy)—N-benzamide;
2-naphthyl-N-(2-phenylethyl)carboxamideN-(4-chlorophenyl)-2-naphthylcarboxamide;
N-(4-bromophenyl)-2-naphthylcarboxamide;
N-(3,4-dimethylphenyl)-2-naphthylcarboxamide;
N-(3-chlorophenyl)-2-naphthylcarboxamide;
(2-chlorophenyl)-N-({[(2-chlorophenyl)amino]thioxomethyl}amino)carboxamide;
N-(4-fluorophenyl)(2-oxochromen-3-yl)carboxamide;
2-(2-1,2,3,4-tetrahydroisoquinolyl)-5-(trifluoromethyl)phenylamine;
(2-aminophenyl)-N-(4-chlorophenyl)carboxamide;
(2-aminophenyl)-N-(4-methylphenyl)carboxamide;
benzo[d]furan-2-yl 4-chloro-3-methylphenyl ketone;
2-[3-(4-chlorophenyl)-1,2,4-oxadiazol-5-yl]phenylamine;
5-(4-chlorophenyl)-2-(4-methylphenyl)-1,3-oxazole;
N-[2-(4-chlorophenyl)-2-oxoethyl](2-fluorophenyl)carboxamide;
2-[4-(tert-butyl)phenyl]-5-fluorobenzo[d]1,3-oxazin-4-one;
(1 Z,3E)-2,3-diaza-4-(4-chlorophenyl)-1-methylthiobuta-1,3-dienylamine;
3-[(3-fluorophenyl)methylthio]-4-hydroimidazolo[1,5-a]pyridine;
7-methylindeno[2,3-b]quinoxalin-1'-one;
N-[4-(phenyldiazenyl)phenyl]acetamide;
(4-chlorophenyl)-N-(4-chlorophenyl)carboxamide;
(2-chlorophenyl)-N-(4-chlorophenyl)carboxamide;
ethyl 4-{5-[(4-chlorophenyl)carbonylamino](1,3,4-thiadiazol-2-ylthio)}-3-oxobutanoate;
N-methyl-2-{5-[(4-methylphenyl)carbonylamino](1,3,4-thiadiazol-2-ylthio)}-3-oxobutanamide;
4-chloro-2-(4-methylphenyl)-5-(methylpyrrolylamino)-2-hydropyridazin-3-one;
N-[5-(tert-butyl)isoxazol-3-yl]-2-methyl-2-{[4-(trifluoromethyl)phenyl]sulfonyl}-propanamide;

4-(1,3-dithiolan-2-yl)-1-[(4-nitrophenyl)methoxy]benzene;
1-nitro-4-[2-(4-nitrophenoxy)ethoxy]benzene;
2,4-diphenyl-1,4,5-trihydropyrimidino[1,2-a]benzimidazole;
2-(4-chlorophenyl)-5,6,7,8,9-pentahydrocyclohepta[1,2-b]pyrimidino[5,4-d]thiophene-4-ylamine;
(1E)-2-amino-1-aza-2-(4-methoxyphenyl)vinyl 2-methoxybenzoate;
6-(2-aminophenyl)-3-(methylethylthio)-2H-1,2,4-triazin-5-one;
(2-fluorophenyl)-N-(2-methyl(6-quinolyl))carboxamide;
N-(4-acetylphenyl)(4-fluorophenyl)carboxamide;
3-amino-6-(4-methylphenyl)thiopheno[2,3-b]pyridine-2-carbonitrile;
phenyl 3-amino-5,6,7-trihydrocyclopenta[1,2-b]furano[4,5-e]pyridine-2-carboxylate;
3-(4-chlorophenyl)-5-phenylpyrazole;
N-{[(2-chlorophenyl)amino]carbonyl}(5-methyl-1-phenylpyrazol-4-yl)carboxamide;
6-chloro-3-(4-nitrophenyl)-4-hydroimidazolo[1,2-a]pyridine;
14-chloro-3-methylphenyl ketone;
N-[2-(3,4-dimethoxyphenyl)ethyl]cyclopropyl-N-[(4-methoxyphenyl)methyl]-carboxamide;
N-[2-(3,4-dimethoxyphenyl)ethyl]-N-{[4-(tert-butyl)phenyl]methyl}-2-furylcarboxamide;
(2-chlorophenyl)-N-(2-(2-pyridyl)ethyl)carboxamide;
(4-methoxyphenyl)-N-(2-(2-pyridyl)ethyl)carboxamide;
(4-methylphenyl)-N-(2-(2-pyridyl)ethyl)carboxamide;
phenyl-N-(2-(2-pyridyl)ethyl)carboxamide;
N-(5,7-dimethylpyridino[3,2-e]pyridin-2-yl)(4-chlorophenyl)carboxamide;
N-(4-fluorophenyl)(2-oxochromen-3-yl)carboxamide;
(4-chlorophenyl)-N-(4-oxobenzo[d]1,3-oxazin-2-yl)carboxamide;
(4-chlorophenyl)-N-(4-oxobenzo[d]1,3-oxazin-2-yl)carboxamide;
(3,4-dichlorophenyl)-N-(4-oxobenzo[d]1,3-oxazin-2-yl)carboxamide;
cyclopropyl-N-(3-phenyl(1,2,4-thiadiazol-5-yl))carboxamide;
3-cyclopentyl-N-indan-5-ylpropanamide;
N-indan-5-yl-2-thienylcarboxamide;
2-furyl-N-indan-5-ylcarboxamide;
N-indan-5-yl(phenylamino)carboxamide;
(cyclohexylamino)-N-indan-5-ylcarboxamide;
[(3-chlorophenyl)amino]-N-indan-5-ylcarboxamide;
[(cyclohexylmethyl)amino]-N-indan-5-ylcarboxamide;
ethyl 4-[(phenylamino)carbonylamino]benzoate;
N-(3,4-dimethylphenyl)[(4-chlorophenyl)amino]carboxamide;
N-(3,4-dichlorophenyl)[(4-methylphenyl)amino]carboxamide;
N-(3,4-dimethylphenyl)[(3-chlorophenyl)amino]carboxamide;
N-(4-ethoxyphenyl)[(4-chlorophenyl)amino]carboxamide;
[(4-chlorophenyl)amino]-N-cyclohexylcarboxamide;
2-[(1E)-2-(4-chlorophenyl)vinyl]benzo[d]1,3-oxazin-4-one;
(4-ethylphenyl)-N-[(2-nitrophenyl)methyl]-N-(2-(2-pyridyl)ethyl)carboxamide;
N-(9-anthrylmethyl)-N-(4-ethylphenyl)[(2-fluorophenyl)amino]carboxamide;

The following examples illustrate the preparation of representative pharmaceutical formulations containing a compound of Formula I.

EXAMPLE 7

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules.

EXAMPLE 8

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 9

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

EXAMPLE 10

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 11

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 12

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) | |
| Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 13

A subcutaneous formulation may be prepared as follows:

| Ingredient | Quantity |
| --- | --- |
| Active Ingredient | 5.0 mg |
| Corn Oil | 1.0 mL |

EXAMPLE 14

An injectable preparation is prepared having the following composition:

| Ingredients | Amount |
| --- | --- |
| Active ingredient | 2.0 mg/ml |
| Mannitol, USP | 50 mg/ml |
| Gluconic acid, USP | q.s. (pH 5–6) |
| water (distilled, sterile) | q.s. to 1.0 ml |
| Nitrogen Gas, NF | q.s. |

EXAMPLE 15

A topical preparation is prepared having the following composition:

| Ingredients | grams |
| --- | --- |
| Active ingredient | 0.2–10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 16

| Sustained Release Composition | | | |
| --- | --- | --- | --- |
| Ingredient | Weight Range (%) | Preferred Range (%) | Most Preferred |
| Active ingredient | 50–95 | 70–90 | 75 |
| Microcrystalline cellulose (filler) | 1–35 | 5–15 | 10.6 |
| Methacrylic acid copolymer | 1–35 | 5–12.5 | 10.0 |
| Sodium hydroxide | 0.1–1.0 | 0.2–0.6 | 0.4 |
| Hydroxypropyl methylcellulose | 0.5–5.0 | 1–3 | 2.0 |
| Magnesium stearate | 0.5–5.0 | 1–3 | 2.0 |

The sustained release formulations of this invention are prepared as follows: compound and pH-dependent binder and any optional excipients are intimately mixed(dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl, methylcellulose, cationic methacrylate copolymers (dimethylaminoethyl methacrylate/methyl-butyl methacrylate copolymers—Eudragit® E—Röhm Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400–600 mg, 650–850 mg, and 900–1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 17 pGL3 Luciferase Assay

This example shows the effect of the compounds of the invention on ABCA-1 gene expression, using the pGL3 luciferase reporter vector system (Promega, Madison, Wis.) to create a recombinant plasmid to measure reporter gene expression under control of the ABCA-1 promoter.

Construction of Reporter Plasmids:

Plasmid pGL3-Basic (Promega, Madison, Wis.; Cat. #E1751) was used as a control plasmid containing the promoterless luciferase gene. The reporter construct containing the ABCA-1 promoter and luciferase gene was made by cloning a genomic fragment from the 5' flanking region of the ABCA-1 gene (HAPR1 5' promoter, corresponding to nucleotides 1080–1643 of SEQ ID NO: 3) into the SacI site of the GL3-Basic plasmid to generate plasmid GL-6a. Next, plasmid GL-6a was digested with SpeI and Acc65I. A BsiWI-SpeI fragment excised from a lambda subclone, representing the ABCA-1 genomic sequence corresponding to nucleotides 1–1534 of SEQ ID NO: 3 was ligated into the remaining vector/ABCA-1 promoter fragment produced by this digestion. The resultant plasmid, pAPR1, encodes the luciferase reporter gene under transcriptional control of 1.75 kb of the human ABCA-1 promoter sequence.

Transfection of Reporter Constructs: The above-described control or pAPR1 plasmid was transfected into confluent cultures of RAW 264.7 cells maintained in DMEM containing 10% fetal bovine serum. Each well of a 12 well dish was transfected for 5 hours with either pGL3-Basic, pGL3-Promoter or pAPR1 DNA (1 $\mu$g), luciferase plasmid DNA (1 $\mu$g), and 12 $\mu$l of Geneporter reagent (Gene Therapy Systems, San Diego, Calif.; Cat. #T201007). In addition, 0.1 $\mu$g of pCMVP plasmid DNA (Clontech, Palo Alto, Calif., Cat. #6177–1) was added as a control for transfection efficiency. After 5 hours, the culture medium was replaced with serum-free DMEM/BSA in the presence of or absence of acetylated LDL (100 $\mu$g/ml) and incubated for 24 hours.

For added convenience in high throughput screening, cultured cells can be stably transfected with reporter plasmids using the following procedure. First, 5×10$^6$ RAW 264.7 cells are transfected for 5 hours in a 60 mm dish with 9 $\mu$g of the pAPR1 plasmid and pCMVscript (Stratagene, LaJolla, Calif.) in 10 ml of serum-free DMEM with 50 $\mu$l Geneporter transfection reagent (Gene Therapy Systems, San Diego, Calif.). Subsequently, the transfection medium is replaced with complete medium and the cells incubated overnight at 37° C. Subsequently, the cells are transferred to separate dishes at dilutions ranging from 1:5 to 1:1000 and incubated in selection medium containing 800 $\mu$g/ml G418 (Life Technologies, Bethesda, Md.) for 20 days. Visible colonies are picked, expanded, and assayed for luciferase activity as described below. Using this method, five clonal cell lines positive for luciferase activity were identified for use in high throughput assays.

Luciferase Assay: Following transfection, the cells in each well were lysed in 70 $\mu$l of 1× cell lysis reagent (Promega, Madison, Wis., Cat. #E3971), subjected to one freeze-thaw cycle, and the lysate cleared by centrifugation for 5 minutes at 12,000 g. After centrifugation, 100 $\mu$l of luciferase assay reagent (Promega, Madison, Wis.; Cat. #E1501) was added to 10 $\mu$l of lysate. The luciferase activity of each lysate was measured as light units using a luminometer. Additionally, the $\beta$-galactosidase activity of each lysate was measured using the chemiluminescent assay reagents supplied in the Galacto-light kit according to the manufacturer's instructions (Tropix Inc., Bedford, Mass.: Cat. #BL100G). The normalized luciferase activity for each lysate was determined by dividing the luciferase activity value by the determined $\beta$-galactosidase value and reported as relative light units.

The compounds of the invention demonstrated increased ABCA-1 gene expression in this assay.

EXAMPLE 18 mRNA Assays

Modulation of expression of ABCA-1 mRNA levels by the compounds of the invention is determined in the following assays.

Quantitative PCR

Cultures of THP were grown to subconfluence in DMEM/10% FBS before replacement with DMEM/BSA and the indicated additive for 24 or 48 hours. RNA using standard methods.

Quantitative PCR was carried out using the GeneAmp 5700 Sequence Detection System (Perkin-Elmer Applied Biosystems, Foster City, Calif.). Briefly, 500 ng of DNAse-treated mRNA was reverse transcribed using random hexamer primers at 2.5 $\mu$M. Approximately 5% of this reaction was amplified by PCR using the SYBR green core kit (PE Applied Biosystems, Foster City, Calif.; Cat. #4304886) and human ABCA-1 primers LF:5'-CCTCTCATTACACAAAAACCAGAC (SEQ ID NO: 11) and LR:5'-GCTTTCTTTCACTTCTCATCCTG (SEQ ID NO: 12) to yield an 82 bp fragment corresponding to nucleotides 7018–7099 of human ABCA-1. PCR cycle conditions were as follows: 10 minutes 95° C.; followed by 40 cycles of 95° C., 15 seconds; and 60° C., 60 seconds. The mRNA in each sample was quantitated by detecting the increase in fluorescence caused by SYBR green binding to the double-stranded amplification product generated during each PCR cycle. All samples were run in triplicate and normalized against $\beta$-actin mRNA, amplified in parallel reactions with primers actin F:5'-TCACCCACACTGTGCCATCTACGA (SEQ ID NO: 54) and actin B:5'-CAGCGGAACCGCTCATTGCCAATGG (SEQ ID NO: 55). Standard curves were run for both ABCA-1 and $\beta$-actin on the same PCR plate.

Changes in mRNA levels were also determined using RAW 264.7 cells with a QuantiGene® Expression Kit from Bayer.

The compounds of the invention modulate expression of ABCA-1 mRNA levels in this assay.

EXAMPLE 19

Lipid Efflux Assay

This example demonstrates that enhanced expression of ABCA-1 protein in the plasma membrane is associated with lipid efflux.

Cell-surface labeling and immunoprecipitation is used to determine whether increased expression of ABCA-1 protein in the plasma membrane is correlated with an increase in cholesterol efflux. The relative amount of ABCA-1 on the cell surface is determined by cross-linking surface proteins on intact cells with the membrane-impermeable agent sulfo-NHS-biotin, followed by the steps of membrane solubilization, immunoprecipitation with ABCA-1 antibody, SDS-PAGE, and detection with streptavidin.

Cell Culture: Fibroblasts are cultured under control conditions and conditions known to increase cholesterol efflux (Oram, et al., J. Lip. Res., 40: 1769–1781 (1999)). Control cells are grown to confluence in DMEM/10% FBS and then incubated in DMEM/BSA for 18 hours with no additives (control). cAMP-treated cells are grown to confluence in DMEM/10% FBS and then incubated in DMEM/BSA for 18 hours with 1 mM 8-Br-cAMP(cAMP). Cholesterol-loaded cells are grown to confluence in DMEM/10% FBS and then incubated in DMEM/BSA for 48 hours with 30 µg/ml cholesterol plus 18 hours with no additives (cholesterol). Cholesterol-loaded cells treated with cAMP are grown to confluence in DMEM/10% FBS and then incubated in DMEM/BSA for 48 hours with 30 µg/ml cholesterol plus 18 hours with 1 mM 8-Br-cAMP (cholesterol+cAMP).

Cell-Surface Labeling: For selective labeling of plasma membrane ABCA-1, the cells are incubated for 30 minutes at 0° C. with PBS containing 1 mg/ml sulfo-NHS-biotin (Pierce, Rockford, Ill.; Cat. #21217) to biotinylate cell-surface proteins (see Walker et al., Biochemistry, 50:14009–14014 (1993)).

Immunoprecipitation: Rabbit antiserum for ABCA-1 is raised against a synthetic peptide corresponding to the deduced peptide KNQTVVDAVLTSFLQDEKVKES located at the C-terminus of human ABCA-1. Immunoprecipitation is performed by solubilizing the cells in PBS containing 1% Triton X-100 (Sigma, St. Louis, Mo.) and protease inhibitors leupeptin (1 mM), pepstatin (1 mM), and aprotinin (1 mM). The cell extract is incubated overnight at 4° C. with anti-ABCA-1 antiserum at 1:200 dilution followed by an additional 1 hour incubation with 5 µl proteinA-coated magnetic beads (Dynal, Lake Success, N.Y.; Cat. #1001.01). The antibody-antigen complex is sedimented with a magnet, the beads are ished twice with 1% Triton-X/PBS, and the proteins are eluted with 1% acetic acid.

Detection of ABCA-1 Protein: The eluted biotinylated proteins are subjected to SDS-PAGE (6% gel; 150V, 5 hours) and transferred to nitrocellulose membrane (200 mA, 18 hours). The nitrocellulose is probed with streptavidin-horse radish peroxidase (Amersham Pharmacia, Piscataway, N.J.; Cat. #RPN 1231) diluted 300-fold and detected by enhanced chemiluminescence labeling (ECL) according to vendor's protocol (Amersham Pharmacia, Piscataway, N.J.). To test for possible biotinylation of intracellular proteins, the post-immunoprecipitation supernatant is treated with a mouse monoclonal antibody to the intracellular protein β—COP and immunoprecipitated biotinylated β-COP is assayed by streptavidin blotting.

EXAMPLE 20

The ability of the compounds of the invention to stimulate cholesterol efflux from cells is determined in the following assay.

RAW 264.7 cells were loaded with cholesterol as described in Smith et al., J. Biol. Chem., 271:30647–30655 (1996). Briefly, semi-confluent cells plated in 48-well dishes were incubated in 0.2 ml of DMEM supplemented with 4.5 g/L glucose, 0.1 g/L sodium pyruvate and 0.584 g/L of glutamine, 10% fetal bovine serum, 50 µg/ml acetylated low density lipoprotein (AcLDL) and 0.5 µCi/ml of [$^3$H]-cholesterol. After 18 hr, cells were washed two times with PBS containing 1% BSA and incubated overnight (16–18 hours) in DMEM/1% BSA to allow for equilibration of cholesterol pools. The cells were then rinsed four times with PBS/BSA and incubated for one hour at 37° C. with DMEM/BSA. Efflux medium (DMEM/BSA) containing either albumin alone (control), albumin plus HDL (40 µg protein/ml), or albumin plus apo A-I (20 µg/ml, Biodesign International, Kennebunk, Me.) was added and the cells were incubated for 4, 24, or 48 hours.

Cholesterol efflux was measured by removing the medium, washing the cell layer and extracting the cells. Cellular radioactivity was measured by scintillation counting after solubilization in 0.5 ml of 0.2M NaOH (Smith et al., J. Biol. Chem., 271:30647–30655 (1996)) or extraction in hexane:isopropanol (3:2 v/v) as described in Francis et al., J. Clin. Invest., 96, 78–87 (1995). The labelled phospholipid remaining in the medium was also determined by liquid scintillation counting. The efflux of cholesterol was expressed as the percentage of tritiated lipid counts in the medium over the total tritiated lipid counts recovered from the cells and medium (cpm medium/cpm (medium+lysate)× 100).

Cholesterol efflux was also determined in THP cells. Replicate cultures of THP cells were plated in 48 well dishes using the method described (see Kritharides et al Thrombo Vasc Biol 18, 1589–1599,1998). Cells were plated at an initial density of 500,000 cells/well. After addition of PMA (100 ng/ml), the cultures were incubated for 48 hr at 37 C. The medium was aspirated and replaced with RPMI-1640 medium containing 2 mg/ml of FAFA, 50 µg/ml of acetylated LDL and 3 µCi/ml of radiolabeled cholesterol. After an overnight incubation, the medium was aspirated, the wells washed extensively with PBS. 0.2 ml of RPMI-1640 medium containing 2 mg/ml of FAFA was added to each well. The compound of interest was added to a final concentration of 10 µM. After 4 hr, Apolipoprotein A1 (10 µg/ml) was added to some wells and the cultures incubated for 24 hr. The medium was harvested and assayed for radioactivity. The amount of radioactivity in the cell layer was ascertained by adding 0.2 ml of 2 M NaOH and counting the lysed cells. The percent cholesterol efflux was calculated as described above.

The compounds of the invention stimulate cholesterol efflux in this assay.

EXAMPLE 21

The relationship between ABCA-1 expression and HDL levels is determined in the following in vivo assay.

Candidate compounds that increase ABCA-1 expression in vitro and are pharmacologically active and available in vivo are administered daily at a predetermined dosage to 7 week old male C57B1/6 mice either by intraperitoneal injection or by gavage in 10% Cremaphore (BASF)/saline.

Three to 4 hours after the final injection, fasted EDTA-plasma and appropriate tissues are collected for analysis. Plasma HDL is isolated by phosphotungstic acid precipitation (Sigma) and HDL cholesterol, total cholesterol and triacylglycerols are determined enzymatically using kits (Roche Diagnostics). Changes to HDL cholesterol and size are further analyzed by FPLC using two Superose 6/30 columns connected in series with cholesterol in the eluted fractions detected enzymatically. In vivo changes in ABCA-1 gene expression are further confirmed by RT-PCR analysis of RNA isolated from candidate tissues.

A correlation between ABCA-1 expression and HDL levels is observed in this assay.

What is claimed is:

1. A method of treating a disease state or condition in a mammal that is alleviable by treatment with an agent capable of increasing ABCA-1 expression, comprising administering to a mammal in need thereof a therapeutically effective dose of a compound of the Formula I:

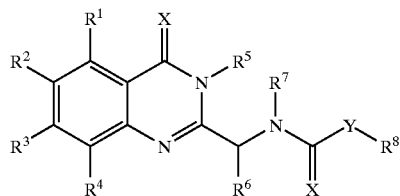

Formula I wherein:
$R^1$, $R^2$, $R^3$ and $R^4$ are independently hydrogen, optionally substituted alkyl, optionally substituted alkenyl, optionally substituted alkynyl, optionally substituted alkoxy, optionally substituted cycloalkyl, acyl, acylamino, acyloxy, optionally substituted amino, aminocarbonyl, cyano, halogen, hydroxy, carboxy, carboxyalkyl, optionally substituted aryl, optionally substituted aryloxy, optionally substituted heteroaryl, optionally substituted heterocyclyl, $SO_2NR^aR^b$, —SO-alkyl, —SO-aryl, —SO-heteroaryl, —$SO_2$-alkyl, $SO_2$-aryl, and trifluoromethyl;
in which $R^a$ and $R^b$ are independently hydrogen, lower alkyl, or cycloalkyl;

$R^5$ is hydrogen, optionally substituted alkyl, optionally substituted alkenyl, optionally substituted alkynyl, optionally substituted cycloalkyl, optionally substituted heterocyclyl, optionally substituted aryl, or optionally substituted heteroaryl;

$R^6$ is hydrogen, optionally substituted alkyl, or optionally substituted cycloalkyl;

$R^7$ is hydrogen, optionally substituted alkyl, optionally substituted alkenyl, optionally substituted alkynyl, optionally substituted cycloalkyl, optionally substituted heterocyclyl, optionally substituted aryl, or optionally substituted heteroaryl;

$R^8$ is optionally substituted alkyl, optionally substituted alkenyl, optionally substituted alkynyl, optionally substituted cycloalkyl, optionally substituted heterocyclyl, optionally substituted aryl, or optionally substituted heteroaryl;

X is independently oxygen or sulfur; and

Y is oxygen or —$NR^9$, in which $R^9$ is hydrogen or lower alkyl.

2. The method of claim 1, wherein $R^1$, $R^2$ and $R^4$ are hydrogen, $R^3$ is hydrogen or halogen, and X is oxygen.

3. The method of claim 2, wherein $R^6$ and $R^7$ are independently optionally substituted lower alkyl, and Y is —$NR^9$ which $R^9$ is hydrogen.

4. The method of claim 3, wherein $R^5$ is optionally substituted lower alkyl or optionally substituted aryl.

5. The method of claim 4, wherein $R^8$ is optionally substituted lower alkyl.

6. The method of claim 5, wherein $R^3$ is hydrogen, $R^5$ is n-propyl, $R^6$ is ethyl, $R^7$ is benzyl, and $R^8$ is 2,4,4-trimethylpentyl, namely 3,5,5-trimethyl hexanoic acid benzyl~1-(4-oxo-3-propyl-3,4-dihydro-quinazolin-2-yl)-propyl]-amide.

7. The method of claim 4, wherein $R^5$ is optionally substituted aryl.

8. The method of claim 7, wherein $R^5$ is optionally substituted phenyl or optionally substituted naphthyl, and $R^6$ is methyl or ethyl.

9. The method of claim 8, wherein $R^7$ is n-propyl, 3-methylbutyl, 2-methoxyethyl, or benzyl.

10. The method of claim 9, wherein $R^5$ is naphthyl, 3,4-dimethylphenyl, 4-methylphenyl, or 4-chlorophenyl.

11. The method of claim 10, wherein $R^8$ is n-butyl, naphthyl, 2,6-dimethylphenyl, 2-methylphenyl, 3-fluorophenyl, 4-methylphenyl, 4-chlorophenyl, 3-trifluoromethylphenyl, 3-methoxyphenyl, 4-methoxyphenyl, or 2,4-difluorophenyl.

12. The method of claim 1, wherein the disease state or condition is coronary artery disease or atherosclerosis.

13. The method of claim 1, wherein said increased ABCA-1 expression provides elevated serum levels of HDL cholesterol.

14. The method of claim 1, wherein said increased ABCA-1 expression promotes cholesterol efflux from cells of said mammal.

15. A method of treating a disease state or condition in a mammal that is alleviable by treatment with an agent capable of increasing ABCA-1 expression, comprising administering to a mammal in need thereof a therapeutically effective dose of a compound of the Formula III:

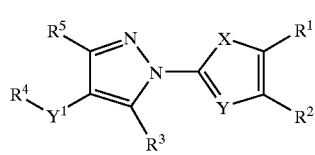

Formula III wherein:
$R^1$ and $R^2$ are independently hydrogen, optionally substituted lower alkyl, optionally substituted cycloalkyl, optionally substituted alkoxy, optionally substituted heterocyclyl, optionally substituted aryl, optionally substituted heteroaryl, or —$CO_2R$, in which R is hydrogen, optionally substituted lower alkyl, or optionally substituted aryl;

$R^3$ and $R^5$ are hydrogen, trifluoromethyl, optionally substituted lower alkyl, or optionally substituted cycloalkyl;

$R^4$ is optionally substituted alkyl, optionally substituted cycloalkyl, optionally substituted heterocyclyl, optionally substituted aryl, or optionally substituted heteroaryl, $Y^1$ is —$N(R^7)$—, —$N(R^7)$—C(T)—, —C(T)—$N(R^7)$—, —$N(R^7)$—C(T)—$N(R^7)$—, —$N(R^7)SO_2$—, or a covalent bond;

in which $R^7$ is hydrogen, optionally substituted alkyl, or optionally substituted aryl; or $R^4$ and $R^7$ when taken together with the nitrogen to which they are attached represents
—Z—C(O)—$R^8$, in which Z is 1,4-piperazinyl optionally substituted with lower alkyl and $R^8$ is optionally substituted alkyl or optionally substituted aryl;

T is oxygen or sulfur;

X is —$NR^a$—, oxygen, or sulfur; in which $R^a$ is hydrogen, lower alkyl, or cycloalkyl; and Y is nitrogen or C($R^6$)—, in which $R^6$ is hydrogen, hydroxy, halo, optionally substituted lower alkyl, optionally substituted lower alkoxy, optionally substituted cycloalkyl, optionally substituted aryl, optionally substituted heteroaryl, or optionally substituted heterocyclyl.

16. The method of claim 15, wherein X is sulfur and Y is nitrogen.

17. The method of claim 16, wherein $R^1$ and $R^5$ are hydrogen and $R^2$ is substituted aryl.

18. The method of claim 17, wherein $R^3$ is optionally substituted lower alkyl.

19. The method of claim 18, wherein $Y^1$ is —C(T)—N($R^7$)—, in which T is oxygen and $R^7$ is hydrogen.

20. The method of claim 19, wherein $R^4$ is optionally substituted lower alkyl or optionally substituted cycloalkyl.

21. The method of claim 20, wherein $R^2$ is 4-methylphenyl, $R^3$ is isopropyl, and $R^4$ is 3-methylbutyl, namely 5-isopropyl-1-(4-p-tolyl-thiazol-2-yl)-1H-pyrazole-4-carboxylic acid (3-methyl-butyl)-amide.

22. The method of claim 20, wherein $R^2$ is 4-methylphenyl, $R^3$ is isopropyl, and $R^4$ is cyclopropyl, namely 5-isopropyl-1-(4-p-tolyl-thiazol-2-yl)-1H-pyrazole-4-carboxylic acid cyclopropylamide.

23. The method of claim 20, wherein $R^2$ is 4-methylphenyl, $R^3$ is isopropyl, and $R^4$ is 1-phenylethyl, namely 5-isopropyl-1-(4-p-tolyl-thiazol-2yl)-1H-pyrazole-4-carboxylic acid (1-phenyl-ethyl)-amide.

24. The method of claim 20, wherein $R^2$ is 4-methoxyphenyl, $R^3$ is ethyl, and $R^4$ is 2-furanylmethyl, namely 5-ethyl-1-[4-(4-methoxyphenyl)-thiazol-2-yl)]-1H-pyrazole-4-carboxylic acid (furan-2-ylmethyl)-amide.

25. The method of claim 20, wherein $R^2$ is 4-methylphenyl, $R^3$ is ethyl, and $R^4$ is 2-furanylmethyl, namely 5-ethyl-1-(4-p-tolyl-thiazol-2-yl)-1-pyrazole-4-carboxylic acid (furan-2-ylmethyl)-amide.

26. The method of claim 20, wherein $R^2$ is 4-methylpheny, $R^3$ is methyl, and $R^4$ is 2-phenylethyl, namely 5-methyl-1-(4-p-tolyl-thiazol-2-yl)-1H-pyrazole-4-carboxylic acid phenethyl-amide.

27. The method of claim 15, wherein the disease state or condition is coronary artery disease or atherosclerosis.

28. The method of claim 15, wherein said increased ABCA-1 expression provides elevated serum levels of HDL cholesterol.

29. The method of claim 15, wherein said increased ABCA-1 expression promotes cholesterol efflux from cells of said mammal.

30. A method of treating a disease state or condition in a mammal that is alleviable by treatment with an agent capable of increasing ABCA-1 expression, comprising administering to a mammal in need thereof a therapeutically effective dose of a compound of the Formula V:

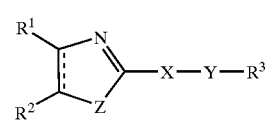

Formula V wherein:

$R^1$ and $R^2$ are independently hydrogen, hydroxy, optionally substitute lower alkyl, optionally substituted alkoxy, optionally substituted aryl, optionally substituted heteroaryl, or —$CO_2R$, in which R is hydrogen, optionally substituted lower alkyl, or optionally substituted aryl; or $R^1$ and the dotted line when taken together with the carbon atom to which they are attached represent carbonyl; or $R^1$ and $R^2$ when taken together with the carbons to which they are attached form an optionally substituted 6-membered carbocyclic aromatic ring when the dotted line is a double bond;

$R^3$ is optionally substituted cycloalkyl, optionally substituted aryl, or optionally substituted heteroaryl;

X is —$NR^4R^5$, —C(T)—$NR^4$—, —$NR^4$C(T)—, —$NR^4CSO_2$—, or —$NR^4$—C(T)$NR^4$;

in which T is oxygen or sulfur, $R^4$ is hydrogen, optionally substituted lower alkyl, or optionally substituted cycloalkyl, and $R^5$ is optionally substituted aryl;

Y is optionally substituted lower alkylene or a covalent bond;

Z is oxygen, sulfur, or —NH—; and the dotted line represents an optional double bond.

31. The method of claim 30, wherein X is —$NR^4$C(T)—, in which $R^4$ is hydrogen and T is oxygen, Y is a covalent bond, Z is sulfur, and the dotted line represents a double bond.

32. The method of claim 31, wherein $R^3$ is optionally substituted cycloalkyl or optionally substituted aryl.

33. The method of claim 32, wherein one of $R^1$ and $R^2$ is hydrogen and the other is optionally substituted aryl.

34. The method of claim 33, wherein $R^1$ is phenyl or naphthyl, $R^2$ is hydrogen, and $R^3$ is optionally substituted phenyl.

35. The method of claim 34, wherein $R^3$ is 4-cyanophenyl, 4-hydroxyphenyl, or 3,4-dimethylphenyl.

36. The method of claim 33, wherein $R^1$ is hydrogen, $R^2$ is optionally substituted phenyl, and $R^3$ is optionally substituted cycloalkyl.

37. The method of claim 36, wherein $R^2$ is phenyl, 2-chlorophenyl or 4-fluorophenyl and $R^3$ is cyclopropyl.

38. The method of claim 37, wherein $R^2$ is phenyl, namely cyclopropyl-N-(5-phenyl(1,3-thiazol-2-yl))carboxamide.

39. The method of claim 31, wherein $R^1$ and $R^2$ taken together with the carbons to which they are attached form an optionally substituted 6-membered carbocyclic aromatic ring.

40. The method of claim 39, wherein $R^3$ is optionally substituted aryl or optionally substituted heteroaryl.

41. The method of claim 40, wherein the 6-membered carbocyclic aromatic ring is optionally substituted with halogen, and $R^3$ is 3-cyanopheny, 4-cyanophenyl, or 4-methoxyphenyl.

42. The method of claim 41, wherein the 6-membered carbocyclic aromatic ring is optionally substituted with chloro.

43. The method of claim 40, wherein $R^3$ is optionally substituted heteroaryl.

44. The method of claim 43, wherein the 6-membered carbocyclic aromatic ring is optionally substituted with halogen or lower alkylsulfonyl.

45. The method of claim 43, wherein the 6-membered carbocyclic aromatic ring is substituted with methylsulfonyl at the 6-position, and $R^3$ is 2-thienyl, namely N-[6-(methylsulfonyl)benzothiazol-2-yl]-2-thienylcarboxamide.

46. The method of claim 30, wherein the disease state or condition is coronary artery disease or atherosclerosis.

47. The method of claim 30, wherein said increased ABCA-1 expression provides elevated serum levels of HDL cholesterol.

48. The method of claim 30, wherein said increased ABCA-1 expression promotes cholesterol efflux from cells of said mammal.

* * * * *